(12) United States Patent
Chae et al.

(10) Patent No.: US 7,795,213 B2
(45) Date of Patent: Sep. 14, 2010

(54) METHODS OF CONTACTING β AMYLOID PROTEIN WITH VEGF

(75) Inventors: Chi-Bom Chae, Seoul (KR); Yong Song Gho, Suwon (KR); Seung-Pil Yang, Pohan (KR); Dong-Goo Bae, Pohang (KR); Byung Oh Kwon, Seoul (KR); Sewook Hwang, Pohang (KR)

(73) Assignees: POSCO, Pohang-shi (KR); Postech Foundation, Pohang (KR)

( * ) Notice: Subject to any disclaimer, the term of this patent is extended or adjusted under 35 U.S.C. 154(b) by 646 days.

(21) Appl. No.: 11/548,397

(22) Filed: Oct. 11, 2006

(65) Prior Publication Data
US 2008/0293922 A1    Nov. 27, 2008

Related U.S. Application Data

(63) Continuation-in-part of application No. 10/318,302, filed on Dec. 12, 2002, now abandoned.

(51) Int. Cl.
 *A61K 38/19* (2006.01)
(52) U.S. Cl. .................. 514/12; 530/350
(58) Field of Classification Search ............ None
See application file for complete search history.

(56) References Cited

U.S. PATENT DOCUMENTS

| | | | |
|---|---|---|---|
| 5,194,596 A | 3/1993 | Tisher et al. | |
| 5,332,671 A | 7/1994 | Ferrara | |
| 5,441,050 A | 8/1995 | Thurston et al. | |
| 6,214,569 B1 | 4/2001 | Potter | |
| 6,245,572 B1 | 6/2001 | Wall | |
| 6,472,179 B2 | 10/2002 | Stahl et al. | |
| 2003/0113324 A1* | 6/2003 | Alitalo et al. | 424/145.1 |
| 2005/0222022 A1* | 10/2005 | Greenberg et al. | 514/12 |
| 2008/0025962 A1* | 1/2008 | Hayashi et al. | 424/94.5 |

FOREIGN PATENT DOCUMENTS

| | | |
|---|---|---|
| WO | WO 00/13703 | 3/2000 |
| WO | WO 03/082918 | 10/2003 |
| WO | 2006/059777 | * 6/2006 |

OTHER PUBLICATIONS

Yang 2005 (Neurobiology of Aging 25:283-290.*
Bennett et al., *Neurobiol Aging* 2000;21(2):207-214.
Bohrmann et al., *J Biol Chem* 1999;274(23):15990-15995.
Calhoun et al., *Nature* 1998;395(6704):755-756.
Chang et al., *Brain Res Protoc* 2000;6(1-2):6-12.
de la Torre JC., *Stroke* 2002;33(4):1152-1162.
de Vries et al., *Science* 1992;255(5047):989-991.
DeBlasi et al., *Trends Pharmacol Sci* 1989;10(6):227-229.
Dillon N., *Tibtech* 1993; 11: 167-173.
Dodet B., *Tibtech* 1993;11: 182-189.
Dzau et al., *Tibtech* 1993; 11: 205.
Fairbrother et al., *Structure* 1998;6:637.
Ferrara N. *Am J Physiol Cell Physiol* 2001;280(6):C1358.
Ferrara et al., *Endocrine Reviews* 1992;13(1):18.
Findeis et al., *Tibtech* 1993;11: 202.
Friedmann T., *Tibtech* 1993; 11:156.
Friedmann et al., *Tibtech* 1993; 11:192.
Goldspiel et al., *Clinical Pharmacy* 1993;12:488.
Gitay-Goren et al., *J Biol Chem* 1992;267(9):6093.
Hamazaki H., *J Biol Chem* 1995;270(18):10392.
Hardy et al., *Science* 1992;256(5054):184.
Harrigan et al., *Neurosurgery* 2002;50(3):589.
Hsiao et al., *Science* 1996;274(5284):99.
Hughes et al., *Proc Natl Acad Sci USA* 1998;95(6):3275.
Iwasaki et al., *The EMBO Journal* 1997;16(23):6936.
Jendroska et al., *Acta Neuropathol* (Berl) 1995;90(5):461.
Jin et al., *Proc Natl Acad Sci USA* 2000;97(18):10242.
Jung et al., *International Journal of Experimental Pathology* 2001; 82: 309.
Kalaria RN. *Neurobiol Aging* 2000;21(2):321.
Kalaria et al., *Mol Brain Res* 1998;62(1):101.
Keyt et al., *J Biol Chem* 1996;271(13):7788.
Kokmen et al., *Neurology* 1996;19:154.
Koller et al., *Proc. Natl. Acad. Sci. USA* 1989;86:8932.
Leung et al., *Science* 1989;246:1306.
Lewis et al., *Science* 2001;293(5534):1487.
Marti et al., *Am J Pathol* 2000;156(3):965.
Marti et al., *Proc Natl Acad Sci USA* 1998;95(26):15809.
Matsuzaki et al., *FASEB J* 2001;15(7):1218.
Mitani et al., *Tibtech* 1993;11:162.
Morgan et al., *Annu Rev Biochem* 1993; 63: 191.
Mulligan R., *Science* 1993; 260: 926.
Nabel et al., *Tibtech* 1993; 11: 211.
Ogunshola et al., *J Biol Chem* 2002; 277 (13): 11410.
Oosthuyse et al., *Nature Genet* 2001;28(2):131.
Plate et al., *Nature* 1992; 359(6398):845.
Porteous et al., *Tibtech* 1993; 11: 173.
Schenk et al., *Nature* 1999; 400(6740):173.
Schratzberger et al., *Nature Med* 2000;6(4):405.
Shweiki et al., *Nature* 1992;359(6398):843.
Sikora K., *Tibtech* 1993; 11: 197.
Snowdon et al., *JAMA* 1997;277(10):813.
Soker et al., *Cell* 1998;92(6):735.
Soker et al., *J Biol Chem* 1997; 272(50): 31582.
Sommer B., *Curr Opin Pharmacol* 2002;2(1):87.
Sondell et al., *J Neurosci* 1999;19(14):5731.
Stein et al., *Mol Cell Biol* 1995;15(10):5363.
Strittmatter et al., *Proc Natl Acad Sci USA* 1993;90(17):8098.
Tarkowski et al., *Neurobiol Aging* 2002;23(2):237.
Terman et al., *Biochem Biophys Res Commun* 1992;187(3):1579.

(Continued)

*Primary Examiner*—Daniel E. Kolker
(74) *Attorney, Agent, or Firm*—Joseph H. Kim; JHK Law

(57) ABSTRACT

The present invention relates to a VEGF polypeptide that binds to Aβ. The present invention also relates to a compound that sequesters Aβ. And conversely, the invention relates to a compound that sequesters VEGF. Thus, the present invention also relates to a method of screening for a compound that inhibits the binding of VEGF to Aβ, and thus relates to prevention and treatment of Alzheimer's Disease.

4 Claims, 13 Drawing Sheets

OTHER PUBLICATIONS

Thomas et al., *Nature* 1996;380(6570):168.
Tischer et al., *J Biol Chem* 1991; 266(18): 11947.
Tolstashev et al., *Annu Rev Pharmacol Toxicol* 1993;32:573.
Vassar et al., *Neuron* 2000;27(3):419-422.
Williamson R., *Tibtech* 1993; 11:159.
Wivel N., *Tibtech* 1993; 11:189.
Wu et al., *J Biol Chem* 1987; 262(10): 4429.
Yamada M., *Neuropathology* 2000;20(1):8.
Yankner BA, *Neuron* 1996;16(5):921.
Yu et al., *Neuroscience Letters* 1998; 254:125.
Zhang et al., *J Clin Invest* 2000;106(7):829.
Zijlstra et al., *Nature* 1989; 342: 435.
Keck et al., Disulfide structure of the Heparin Binding Domain in Vasculat Endothelial Growth Factor . . . , Archives of Biochemistry and Biophysics, 344(1): 103-113 (1997).
Cleland et al., Development of poly- . . . , Journal of Controlled Release, 72: 13-24 (2001).
Philo, Current Protocols in Protein Science 20.1.1-20.1.13 (1999).
Awata T. et al. Diabetes 51:1635-1639 (2002).
Heegaard et al. European Journal of Biochemistry 239:850-856 (1996).
Hammad SM et al. Journal of Biological Chemistry 272:18644-18649 (1997).
Jordan-Starck TC et al. Journal of Lipid Research 35:194-210 (1994).
Watson DJ et al. Journal of Biological Chemistry 272:31617-31624 (1997).

\* cited by examiner

SEQUENCE LISTING

```
<160> NUMBER OF SEQ ID NOS: 5

<210> SEQ ID NO 1
<211> LENGTH: 165
<212> TYPE: PRT
<213> ORGANISM: Homo sapiens

<400> SEQUENCE: 1

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95
```

```
Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 2
<211> LENGTH: 55
<212> TYPE: PRT
<213> ORGANISM: Homo sapiens

<400> SEQUENCE: 2

Ala Arg Gln Glu Asn Pro Cys Gly Pro Cys Ser Glu Arg Arg Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Arg Cys Asp Lys Pro Arg Arg
    50                  55

<210> SEQ ID NO 3
<211> LENGTH: 27
<212> TYPE: PRT
<213> ORGANISM: Homo sapiens

<400> SEQUENCE: 3

Cys Lys Asn Thr Asp Ser Arg Cys Lys Ala Arg Gln Leu Glu Leu Asn
1               5                   10                  15

Glu Arg Thr Cys Arg Cys Asp Lys Pro Arg Arg
            20                  25

<210> SEQ ID NO 4
<211> LENGTH: 42
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Arg Gly Ala Ile Ile
            20                  25                  30

Gly Leu Met Val Gly Gly Val Val Ile Ala
        35                  40

<210> SEQ ID NO 5
<211> LENGTH: 62
<212> TYPE: PRT
<213> ORGANISM: Homo sapiens

<400> SEQUENCE: 5

Ala Asp Cys Lys Tyr Lys Phe Glu Asn Trp Gly Ala Cys Asp Gly Gly
1               5                   10                  15

Thr Gly Thr Lys Val Arg Gln Gly Thr Leu Lys Lys Ala Arg Tyr Asn
```

-continued

```
                20                  25                  30
Ala Gln Cys Gln Glu Thr Ile Arg Val Thr Lys Pro Cys Thr Pro Lys
            35                  40                  45

Thr Lys Ala Lys Ala Lys Ala Lys Lys Gly Lys Gly Lys Asp
    50                  55                  60
```

METHODS OF CONTACTING β AMYLOID PROTEIN WITH VEGF

CROSS REFERENCE TO RELATED APPLICATION

This application is a Continuation-In-Part application claiming a priority based on U.S. patent application Ser. No. 10/318,302 filed on Dec. 12, 2002 and claiming priority to and the benefit of Provisional Application No. 60/339,932 filed on Dec. 13, 2001, which are hereby incorporated by reference for all purposes as if fully set forth herein.

BACKGROUND OF THE INVENTION a) Field of the Invention

The present invention relates to a VEGF (Vascular endothelial growth factor) polypeptide that binds to β-amyloid (Aβ). The present invention also relates to a compound that sequesters Aβ. And conversely, the invention relates to a compound that sequesters VEGF. Thus, the present invention also relates to a method of screening for a compound that inhibits the binding of VEGF to Aβ. In addition, the invention relates to a method of preventing and treating Alzheimer's Disease as well as treating excessive angiogenesis.

b) Description of the Related Art

Alzheimer's disease (AD), the most common cause of dementia in elderly people, is a complex disorder of the central nervous system clinically characterized by a progressive loss of cognitive abilities. Pathological hallmarks of AD are extracellular senile plaques, intracellular neurofibrillary tangles, loss of neurons, cerebral amyloid angiopathy, and degeneration of cerebrovasculatures in certain areas of the brain (Marti et al., Proc Natl Acad Sci USA 1998;95(26): 15809-15814; Yamada M., Neuropathology 2000; 20(1): 8-22; Yankner B A, Neuron 1996;16(5):921-932). Aβ (Aβ) is the major component of senile plaques and is derived from the amyloid precursor protein by proteolytic cleavage (Vassar et al., Neuron 2000;27(3): 419-422). Although accumulating evidence suggests that Aβ is a key causative agent of AD (Calhoun et al., Nature 1998;395(6704):755-756; Hardy et al., Science 1992;256(5054):184-185; Hsiao et al., Science 1996;274(5284):99-102; Lewis et al., Science 2001;293 (5534):1487-1491; Schenk et al., Nature 1999;400(6740): 173-177; Sommer B., Curr Opin Pharmacol 2002;2(1):87-92; Thomas et al., Nature 1996;380(6570):168-171), the exact mechanism of neuronal degeneration in AD is not clear. However, it is likely that multiple factors are involved in the development of the disease.

Most cases of AD are accompanied by cerebrovascular pathologies, such as cerebral amyloid angiopathy, endothelial degeneration, and hypoperfusion (de la Torre J C. Stroke 2002;33(4):1152-1162; Kalaria R N. Neurobiol Aging 2000; 21(2):321-330; Kokmen et al., Neurology 1996;46(1):154-159; Snowdon et al., JAMA 1997;277(10):813-817; Thomas et al., Nature 1996;380(6570):168-171). Vascular risk factors linked to cerebrovascular diseases and stroke, such as hypertension, atherosclerosis, diabetes mellitus, and cardiac disease, are known to significantly increase the risk of developing AD. Most of these vascular pathologies cause cerebral ischemia that are commonly present in AD patients. These observations suggest that cerebrovascular dysfunction may play an important role in the neurodegenerative cascade of AD.

Vascular endothelial growth factor (VEGF) is a major regulator of blood vessel function including hyperpermeability, endothelial cell growth, and enhanced glucose transport. VEGF also plays a key role in physiological blood vessel formation and pathological neovascularization such as tumor growth and ischemic diseases (Ferrara N. Am J Physiol Cell Physiol 2001;280(6):C1358-C1366; Harrigan et al., Neurosurgery 2002;50(3):589-598; Plate et al., Nature 1992;359 (6398):845-848; Shweiki et al., Nature 1992;359(6398):843-845; Zhang et al., J Clin Invest 2000;106(7):829-838). Expression of VEGF and its receptor in various organs including brain is upregulated in response to hypoxic or hypoglycemic stress that are present in AD (Marti et al., Proc Natl Acad Sci USA 1998;95(26):15809-15814; Marti et al., Am J Pathol 2000;156(3):965-976; Stein et al., Mol Cell Biol 1995;15(10):5363-5368).

There are also reports of increased levels of VEGF in the cerebrospinal fluid of AD patients and enhanced VEGF immunoreactivity around perivascular astrocytes and walls of cerebral vessels in subjects with AD when compared with elderly controls (Kalaria et al., Brain Res Mol Brain Res 1998;62(1):101-105; Tarkowski et al., Neurobiol Aging 2002;23(2):237-243). Moreover, VEGF was highly expressed in neuronal and glial cells since cerebrovascular pathologies associated with AD cause cerebral ischemia (Kalaria et al., Brain Res Mol Brain Res 1998;62(1):101-105; Tarkowski et al., Neurobiol Aging 2002;23(2):237-243). However, in these reports, the direct interaction and co-localization of VEGF with Aβ were not established.

Recently, it was reported that VEGF has neurotrophic as well as neuroprotective functions against ischemic and glutamate-induced excitotoxic damage (Jin et al., Proc Natl Acad Sci USA 2000;97(18):10242-10247; Matsuzaki et al., FASEB J 2001;15(7):1218-122P; Ogunshola et al., J Biol Chem 2002;277(13):11410-11415; Oosthuyse et al., Nature Genet 2001;28(2):131-138; Schratzberger et al., Nature Med 2000;6(4):405-413; Sondell et al., J Neurosci 1999;19(14): 5731-5740). These studies have raised the possibility that VEGF may be involved in the vascular and neuronal pathology associated with AD. The present application describes the heavy accumulation and co-localization of VEGF with Aβ plaques in the brain of patients with AD. In vitro experiments show that VEGF binds to Aβ with high affinity and is co-aggregated with Aβ. Once bound, VEGF is released from the complex at a very slow rate.

There is a need in the art to provide more accurate and sensitive molecular tool to detect the presence of Aβ formation and aggregation so that neural diseases such as Alzheimer's Disease can be detected early and treated. In addition, there is a need in the art for a compound that inhibits VEGF binding to Aβ so that VEGF is free to carry out its neuroprotective and neurotrophic activity in the brain.

SUMMARY OF THE INVENTION

The present invention relates to a method of inhibiting aggregation of β-amyloid (Aβ), comprising the steps of contacting a VEGF (Vascular endothelial growth factor) with pre-aggregated Aβ and allowing the VEGF to bind to Aβ to inhibit the aggregation of Aβ. In this method, a binding site of the VEGF which binds to Aβ may have the amino acid sequence of SEQ ID NO: 3 and a binding site of Aβ to which the VEGF binds may have the amino acid sequence of SEQ ID NO: 4. This method may be applied to treatment or prevention of the disease selected from the group consisting of neural disease such as Alzheimer's Disease, cancer, atherosclerosis, rheumatoid arthritis, endometriosis, renal disease and obesity.

Further, the present invention relates to a method of reducing cytotoxicity of Aβ, comprising the steps of contacting a VEGF (Vascular endothelial growth factor) with Aβ and allowing the VEGF to bind to Aβ. In this method, a binding site of the VEGF which binds to Aβ may have the amino acid sequence of SEQ ID NO: 3, and a binding site of Aβ to which the VEGF polypeptide binds may have the amino acid sequence of SEQ ID NO: 4.

Further, the present invention relates to a method of improving VEGF deficiency, comprising the steps of preventing the VEGF (Vascular endothelial growth factor) from binding to Aβ or pre-aggregated Aβ, using an inhibitor, resulting that the concentration of soluble VEGF is maintained to high level. The inhibitor may be selected from the group consisting of catechins such as epicatechin (EC), epicatechin gallate (ECG), epigallocatechin (EGC) and epigallocatechin gallate (EGCG), heparin, heparin related molecules, PGG (pentagalloyl glucose), tannic acid, glycosaminoglycan chain containing compounds, and triamterene. In this method, a binding site of the VEGF which binds to aggregated Aβ may have the amino acid sequence of SEQ ID NO: 3 and a binding site of aggregated Aβ to which the VEGF binds may have the amino acid sequence of SEQ ID NO: 4. This method may be applied to protection of cranial nerve and neurons.

The invention is also directed to a polypeptide that is designed based on VEGF polypeptide, which binds to and absorbs free floating Aβ, thereby rendering Aβ unavailable for aggregation. And conversely, in another embodiment, the invention is directed to a polypeptide that is designed based on Aβ sequence, which is used to sequester and inactivate VEGF where it would be beneficial to remove VEGF from the environment, in order to treat or prevent diseases that arise from excessive angiogenesis, such as cancer, atherosclerosis, rheumatoid arthritis, endometriosis, renal disease or obesity, among others.

In particular, the invention is directed to a β-amyloid binding polypeptide (β-ABP) that specifically binds heparin and Aβ, wherein the polypeptide is not SEQ ID NO:5. The polypeptide may have at least 85% sequence identity to SEQ ID NO:3, at least 90%, 95%, or at least 97% sequence identity to SEQ ID NO:3. In particular, the polypeptide is represented by SEQ ID NO:3, and may have added or subtracted about 5 amino acids from either the N-terminal or C-terminal end. Moreover, the polypeptide may specifically bind to a region on Aβ that is from about Gly residue at position 25 to about Met residue at position 35 of SEQ ID NO:4.

The polypeptide may have a binding affinity for Aβ represented by a dissociation constant of about 10 nM, 1 nM or 100 pM.

The present invention is also directed to an antibody that specifically binds to the polypeptide described above. The antibody may be a monoclonal antibody that is specific for the above described polypeptide.

The present invention is directed to an isolated nucleic acid encoding the polypeptide described above. Further, the invention is directed to an expression vector comprising the nucleic acid. Still further, the invention is directed to a host cell comprising the expression vector.

The present invention is also directed to a method of preventing binding between Aβ and endogenous VEGF, comprising: (a) generating a recombinant viral or plasmid vector comprising a DNA sequence encoding VEGF polypeptide operatively linked to a promoter; and (b) administering the viral or plasmid vector to a patient in need thereof, such that expression of said DNA sequence within a brain results in binding between Aβ and VEGF polypeptide.

In yet another embodiment, the invention is directed to a method of inactivating endogenous VEGF in a region of excessive angiogenesis, comprising: (a) generating a recombinant viral or plasmid vector comprising a DNA sequence encoding Aβ polypeptide operatively linked to a promoter; and (b) administering the viral or plasmid vector to a patient in need thereof, such that expression of said DNA sequence at the site of excessive angiogenesis results in binding between the Aβ polypeptide and endogenous VEGF.

In still another embodiment, the invention is directed to a method of determining binding of VEGF polypeptide to Aβ comprising: (a) providing VEGF to a sample suspected of containing Aβ; and (b) detecting binding of VEGF to the Aβ, if Aβ is present in the sample.

In this method the polypeptide may bind to pre-aggregated Aβ. Further, the polypeptide may bind to extracellular plaques. Further in this method, the polypeptide is heparin binding domain of VEGF. And still further, the polypeptide is substantially C-terminal half of the heparin binding domain.

Another embodiment of the invention is directed to a method of diagnosing a disease that is indicated by presence of amyloid plaques, comprising: (a) providing a sample tissue that is suspected of having amyloid plaques; (b) contacting said sample tissue with a VEGF polypeptide, which is capable of specifically binding to Aβ; and (c) detecting the binding of said polypeptide with said amyloid plaques, wherein binding indicates diseased state.

In this method, VEGF polypeptide may be β-amyloid binding polypeptide (β-ABP). Further, the polypeptide may be labeled. And still further, in the method described above, in step (c), said detecting is carried out by detecting a ligand which specifically binds to either said VEGF polypeptide, Aβ, or VEGF polypeptide/Aβ complex, wherein said ligand is labeled.

The present invention is also directed to a diagnostic kit comprising: (a) a container comprising a VEGF polypeptide that specifically binds Aβ; (b) a first ligand that specifically binds to said VEGF polypeptide, Aβ, or polypeptide/Aβ complex; (c) a labeled second ligand that specifically binds to said first ligand; and (d) instructions for its use.

The invention is directed to a method of preventing binding between VEGF and Aβ, comprising providing a compound which inhibits the interaction between VEGF and Aβ. In this method, the compound is provided to a mammal suffering from a disease indicated by formation of amyloid plaques. The compound may be a monomer or polymer comprising sugar backbone with phenol or sulfate substituent. Further, the compound may be a catechin or a catechin phenol compound.

In yet another embodiment, the invention is directed to a method of screening for a compound which inhibits VEGF/Aβ binding, comprising: (a) contacting a compound with a sample containing VEGF and Aβ; (b) determining level of VEGF and Aβ binding under conditions in which VEGF and Aβ normally specifically bind to each other; (c) determining level of VEGF and Aβ binding, in the presence of said compound; and comparing the level of VEGF and Aβ binding described in parts (a) and (b), wherein if said level is lower in (c) than in (b), then said compound is an inhibitor of VEGF/Aβ binding.

The invention is further directed to a method of treating Alzheimer's Disease comprising administering to a person in need thereof a therapeutically effective amount of a compound which inhibits binding between VEGF and Aβ.

The invention is also directed to an isolated molecule comprising Aβ polypeptide, which is capable of binding VEGF to form a nonfunctional complex comprising: (a) a first polypeptide component comprising an amino acid sequence comprising the Aβ polypeptide which binds to VEGF; and (b) a multimerizing component.

The invention directed to a method for forming a nonfunctional complex of VEGF comprising contacting a sample suspected of containing VEGF with the molecule described above.

The invention is directed to an isolated molecule comprising VEGF polypeptide, which is capable of binding Aβ to form a nonfunctional complex comprising: (a) a first polypeptide component comprising an amino acid sequence comprising the VEGF polypeptide, which binds to Aβ polypeptide; and (b) a multimerizing component.

Still further, the invention is directed to a method for forming a nonfunctional complex of Aβ comprising contacting a sample suspected of containing Aβ with the molecule described above.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
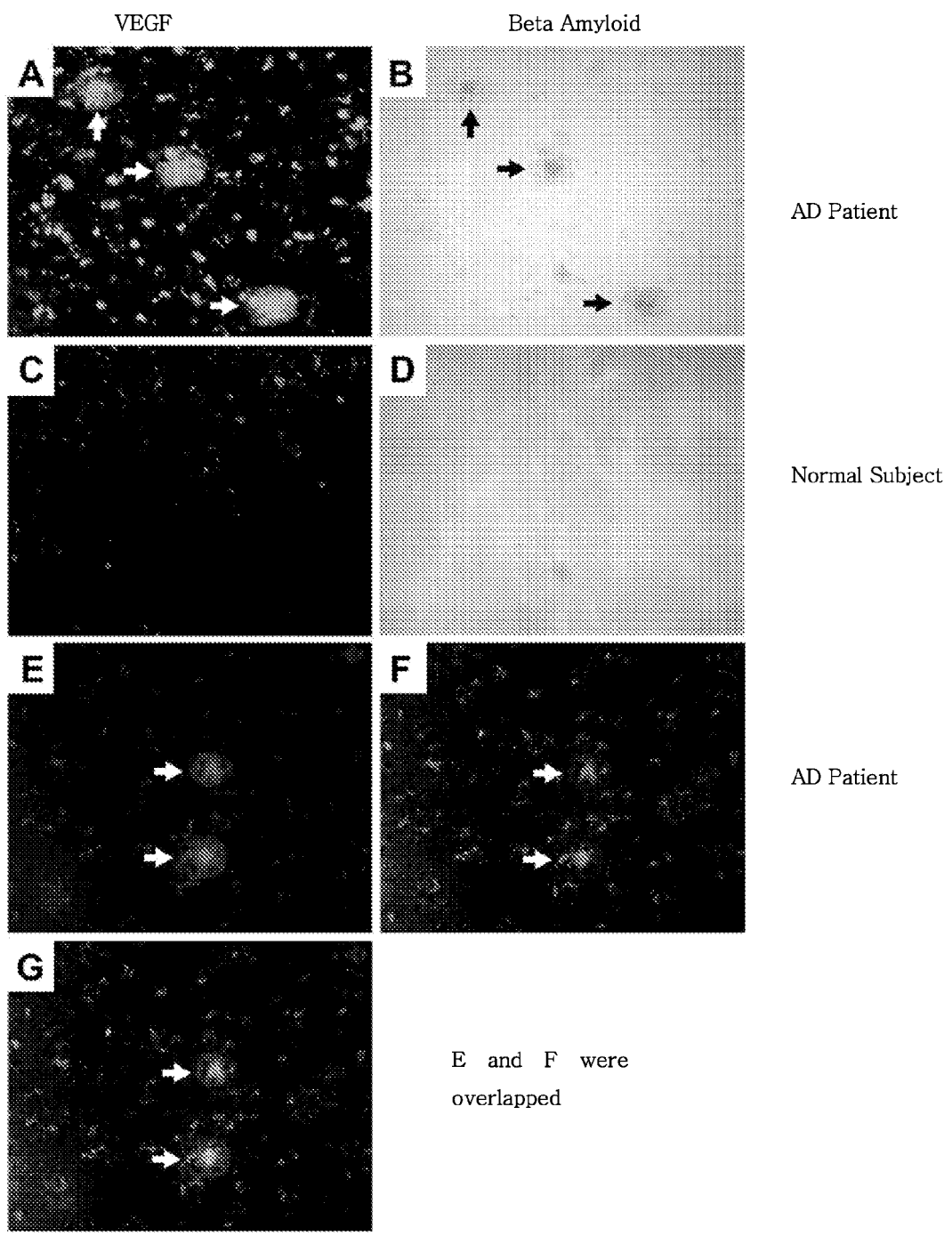
FIGS. 1A-1G show co-localization of Aβ and VEGF in the cerebral cortex of human subjects with AD. Brain sections of AD patient (70 years old, male, Braak stage VI, A, B) and an elderly normal subject (85 years old, male, C, D) were stained with VEGF antibody (A, C) and Congo Red (B, D). Arrows indicate congophilic plaques. Section of another AD patient (80 years old, male, Braak stage VI) was double immunostained with Aβ antibody (E) and VEGF antibody (F), and images were merged (G). The sites indicated by arrows are also stained by Congo Red (data not shown). Note the heavy staining of VEGF and also the matching pattern between the two. Magnification: 400×. Representative data from of elderly normal subjects (n=4) and AD patient (n=7) are shown.

In the present application, "a" and "an" are used to refer to both single and a plurality of objects.

The invention provides solutions to the above-mentioned problems. The present invention is based on the surprising discovery that VEGF (Vascular endothelial growth factor) polypeptide binds specifically to β-amyloid (Aβ). Particular fragments of VEGF and Aβ that bind to each other have been elucidated. And since VEGF co-accumulates with Aβ plaque, the present invention is directed to assaying for the presence of aggregated Aβ or plaques by using either labeled VEGF polypeptide or antibody that specifically binds to VEGF polypeptide/Aβ complex. Thus, the invention is directed to a method of diagnosing Alzheimer's Disease or any other disease that is characterized by the presence of amyloid plaques.

In the present invention, it is found that the VEGF binds to pre-aggregated Aβ, and inhibits the aggregation of Aβ. Therefore, by such biding of the VEGF to pre-aggregated Aβ, the disease that is characterized by the presence of aggregated Aβ or amyloid plaques, such as Alzheimer's Disease, cancer, atherosclerosis, rheumatoid arthritis, endometriosis, renal disease and obesity, can be treated or prevented. Further, in the present invention, it is also found that the VEGF binds to Aβ, to reduce cytotoxicity of Aβ. Furthermore, in the present invention, it is also found that once the aggregation of Aβ occurs, the VEGF binds to aggregated Aβ or amyloid plaques to be co-aggregated, resulting in reducing the concentration of the available (soluble) VEGF which can exhibit their original functions. Therefore, to maintain the concentration of soluble VEGF to high level, it is necessary to inhibit the VEGF from binding to pre-aggregated Aβ or amyloid plaques. By such inhibition for the binding of VEGF to Aβ or pre-aggregated Aβ, the effect of the cranial nerve and neuron protection through the soluble VEGF can be improved. In this invention, effective inhibitors for the binding of VEGF to aggregated Aβ are provided, such as catechins including EC, ECG, EGC, and EGCG, heparin, heparin related molecules, PGG, tannic acid, glycosaminoglycan chain containing compounds, and triamterene.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In one aspect, the polypeptide variants of the present invention may contain any number of amino acids or alterations of amino acids in the non-Aβ binding region or non-VEGF binding region of a polypeptide, including substitutions and/or insertions and/or deletions in any other region of the polypeptide molecule, so long as the polypeptide variant includes a sequence that is at least about 70%, 75%, 80%, 85%, 90%, 95%, 96%, 97%, 98% or 99% identical to the polypeptide sequence represented by SEQ ID NO:3 or SEQ ID NO:4, and the presence of the variations do not hinder the specific binding of the VEGF polypeptide to Aβ and the Aβ polypeptide to VEGF.

As used herein, "β-amyloid binding polypeptide" or "β-ABP" refers to a polypeptide that specifically binds to Aβ and has at least about 70%, 75%, 80%, 85%, 90%, 95%, 96%, 97%, 98%, 99% or 100% identity to the polypeptide sequence represented by SEQ ID NO:3. In particular, β-ABP binds to a region of Aβ beginning at about residue 25 to about residue 35. In addition, β-ABP may have added or subtracted from each end, N-terminus or C-terminus, about 0 to 10 amino acids, about 0 to 5, or from 0 to 4 or from about 0 to 3 or from 0 to 2 or from 0 to 1 amino acids from the core polypeptide of SEQ ID NO:3.

As used herein, "Aβ polypeptide" refers to a polypeptide that is derived from Aβ, but which is not limited to the specific sequence from the Aβ. It is understood that various mutations and conservative amino acid changes are tolerable, as well as certain non-conservative amino acid changes, so long as the polypeptide binds to VEGF. Fragments and certain glycosylations are also permitted, indeed any change at all to the Aβ polypeptide is permitted so long as the polypeptide retains the ability to bind to VEGF.

Applicants for the first time discovered that Aβ binds to VEGF, and thus it would be within the purview of a person of skill in the art to make certain variations to the sequence, which retains the capability of binding to Aβ. In particular, when used in a trap construct to form a non-functional complex with VEGF, a variety of Aβ sequences may be used, including a molecule that has about 70%, 75%, 80%, 85%, 90%, 95%, 96%, 97%, 98% or 99% sequence identity with the polypeptide as shown in SEQ ID NO:4. Further, the polypeptide may be full length 1-40 or 1-42 amino acid Aβ or may include a fragment such as the region 25-35.

As used herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. "High stringency conditions" for the annealing process may involve, for example, high temperature and/or low salt content, which disfavor hydrogen-bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in Current Protocols in Molecular Biology, John Wiley & Sons, N.Y. (1989), 6.31-6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., Molecular Cloning: A Laboratory Manual, Cold Spring Harbor Laboratory Press, Cold Spring N.Y., (1982), at pp. 387-389; see also Sambrook J. et al., Molecular Cloning: A Laboratory Manual, Second Edition, Volume 2, Cold Spring Harbor Laboratory Press, Cold Spring, N.Y. at pp. 8.46-8.47 (1989).

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the Aβ or VEGF binding polypeptides of the present invention. Other post-translational modifications include hydroxylation of proline and lysine, phosphorylation of hydroxyl groups of seryl, tyrosine or threonyl residues, methylation of the a-amino groups of lysine, arginine, and histidine side chains (T. E. Creighton, Proteins: Structure and Molecular Properties, W. H. Freeman & Co., San Francisco, pp. 79-86 (1983)).

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" is defined as an amount of compound capable of preventing binding of VEGF to Aβ or amyloid plaques. In yet another embodiment, the "effective amount" is defined as the neurotrophic and neuroprotective effective amount of VEGF. In other embodiments, "effective amount" may be that amount of VEGF polypeptide that binds to and sequesters free-floating, unaggregated Aβ to render them unavailable for reaction. In yet another embodiment of the invention, "effective amount" may refer to the amount of Aβ polypeptide that is sufficient to bind and sequester VEGF and to render them inactive to further reaction in the instance where angiogenesis is sought to be prevented or lessened.

As used herein, "fragment" refers to a part of a polypeptide, which retains usable and functional characteristics. For example, as used within the context of the present invention, the polypeptide fragment has the function of binding to Aβ, pre-aggregated Aβ, or a plaque comprising Aβ. Furthermore, a fragment of Aβ may bind to VEGF.

As used herein, "GFP" refers to Green Fluorescent Protein.

As used herein, "GST" refers to Glutathione S Transferase.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

As used herein, "immunohistochemistry" refers to a method that measures level of specific protein in a variety of tissues.

As used herein, "immunoprecipitation" refers to a biological method that quantitatively measures expression level of a protein and also qualitatively the interaction between polypeptides.

As used herein, "inhibitor" refers to a molecule that inhibits the binding of VEGF to Aβ.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity, such as in a ligand trap.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "midkine" refers to a heparin-binding, neurotrophic growth factor whose expression occurs mainly in fetus.

As used herein, "purified" or "isolated" molecule refers to biological molecules that are removed from their natural environment and are isolated or separated and are free from other components with which they are naturally associated.

As used herein, "sample" or "biological sample" is referred to in its broadest sense, and includes any biological sample obtained from an individual, body fluid, cell line, tissue culture, or other source which may contain Aβ or VEGF, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art. A tissue biopsy of the brain is a preferred source.

In the biological sample, the polypeptides may also be detected in vivo by imaging. Labels or markers for in vivo imaging of proteins include those detected by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the polypeptide by labeling using conventional techniques.

In addition, a "biological sample" obtained from a patient can be referred to either as a "biological sample" or a "patient sample." It will be appreciated that analysis of a "patient sample" need not necessarily require removal of cells or tissue from the patient. For example, appropriately labeled polypeptides (e.g., antibodies or a polypeptide that binds to Aβ, such as VEGF polypeptide, heparin binding domain of VEGF or β-ABP) can be injected into a subject and visualized (when bound to the target) using standard imaging technology (e.g., CAT, NMR, EPR, PET and the like.) As used herein, "sequence identity", is defined as the percentage of amino acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1.

As used herein, the term "specifically binds" refers to a non-random binding reaction between two molecules, for example between an antibody molecule immunoreacting with an antigen, or a non-antibody ligand reacting with another polypeptide such as Aβ. Moreover, specific binding may also occur between a chemical compound or a small peptide and VEGF.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

As used herein, "VEGF polypeptide" refers to a polypeptide that is derived from VEGF, but which is not limited to the specific sequence from the VEGF. It is understood that various mutations and conservative amino acid changes are tolerable, as well as certain non-conservative amino acid changes, so long as the polypeptide binds to Aβ. Fragments and certain glycosylations are also permitted, indeed any change at all to the VEGF polypeptide is permitted so long as the polypeptide retains the ability to bind to Aβ. In another embodiment, the polypeptide also binds to heparin. It is understood that applicants for the first time discovered that VEGF, and in particular the heparin binding domain, binds to Aβ, and thus it would be within the skill of a person of skill in the art to make certain variations to the sequence which retains the capability of binding to Aβ. VEGF polypeptide includes, but is not limited to, β-ABP. VEGF polypeptide further includes polypeptides having 70%, 75%, 80%, 85%, 90%, 95%, 96%, 97%, 98%, or 99% sequence identity with the polypeptide as shown in SEQ ID NO:1.

Beta-Amyloid Binding Domain of VEGF

VEGF precursor RNA undergoes various alternate RNA splicing events that lead to the production of four mature homodimeric proteins, each monomer having 121, 165, 189 and 206 amino acids (VEGF121, VEGF165, VEGF189 and VEGF206, respectively) (Leung et al., Science 1989;246: 1306-1309; Tischer et al., J. Biol. Chem. 1991;266:11947-11954; Houck et al., Mol. Endocrinol. 1991;5, 1806-1814). Among these, VEGF165 is the most abundantly expressed isoform of VEGF. Among various isoforms, VEGF165, 189 and 206 have heparin-binding domain at the C-terminus and bind to heparin sulfate proteoglycan on the cell surface and extracellular matrix. VEGF121 lacks heparin binding domain and does not bind to heparin sulfate. The role of the heparin binding domain of VEGF appeared to be sequestration of VEGF on target cell surface, for example, endothelial cells and to increase the binding affinity of VEGF to its cell surface receptor (Gitay-Goren et al., J. Biol. Chem. 1992;267, 6093-6098). In fact, VEGF165 has higher binding affinity for its cell surface receptor than VEGF121. Also, VEGF165 has 100 fold more bioactivity than VEGF121 (Keyt et al., J. Biol. Chem. 1996;271:7788-7795).

The receptor binding domain of VEGF is structurally related to platelet-derived growth factor (PDGFβ) and to a family of growth factors, including nerve growth factor (NGF) and transforming growth factor (TGFβ) (Ferrara et al., Endocrinol Rev. 1992;13, 18-32; Murray-Rust et al., Structure 1993;1, 153-159). However, we found that among the several growth factors tested, such as NGF, basic fibroblast growth factor (bFGF), PDGF VEGF and midkine (Yu et al., Neurosci Lett 1998;254, 125-128, for description of midkine), only VEGF and midkine bound to A. Although it would seem that the binding of midkine to A may be through the heparin-binding domain, the heparin-binding domains of VEGF(Fairbrother et al., Structure 1998;6,637-648) and midkine (Iwasaki et al., EMBO J 1997;16, 6936-6947) appear to be sequentially unrelated to each other as evidenced by only a 4% sequence identity between their respective heparin binding domains. The amino acid sequence of the heparin binding domain of midkine is as follows: ADCKYKFENW GACDG-GTGTK VRQGTLKKAR YNAQCQETIR VTKPCTPKTK AKAKAKKGKG KD (SEQ ID NO:5).

The subunits of VEGF are assembled into a dimer by asymmetric association of two homo subunits, and the two heparin-binding domains of VEGF165 are exposed and can be selectively cleaved by plasmin, releasing the 55 amino acid C-terminus heparin-binding domain and 110 amino acid main body of VEGF (Fairbrother et al., Structure 1998;6,637-648).

Figure 5:
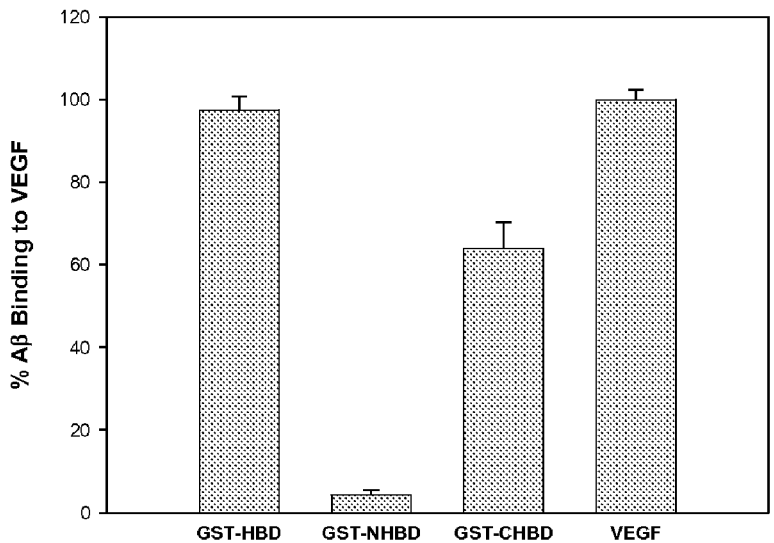
FIG. 5 shows that A binds mostly to the C-terminal (29-55 amino acid) region of the heparin binding domain of VEGF. Aβ binds to C-terminal sub-domain of heparin-binding domain, but not to N-terminal half of heparin-binding domain. All values expressed as mean±SEM. GST-HBD: full heparin-binding domain fused to GST, GST-NHBD: N-terminal half (amino acid 1-29) of heparin-binding domain fused to GST; GST-CHBD: C-terminal half (amino acid 29-55) of heparin-binding domain fused to GST.

The 3-dimensional structure of the 55 amino acid heparin-binding domain has been solved (Fairbrother et al., Structure 1998;6,637-648) and the positively charged side chains of the following residues were suggested to be involved in heparin binding: Arg13, Arg14, Lys15, Lys30, Arg35, Arg39 and Arg46, with potential contributions from Lys52, Arg54 and Arg55. It was suggested that the hexasaccharide units in heparin polymer bind to the positive charges of the heparin-binding domain. We discovered that when the 55 amino acid heparin-binding domain is divided into N-terminal (about 1-29 amino acid) and C-terminal (about 29-55 amino acid) portions, A binds mostly to the C-terminal half (FIG. 5).

The amino acid sequence for VEGF165 is as follows: APMAEGGGQN HHEVVKFMDV YQRSYCHPIE TLVDIFQEYP DEIEYIFKPS CVPLMRCGGC CNDE-GLECVP TEESNITMQI MRIKPHQGQH IGEMSFLQHN KCECRPKKDR ARQENPCGPC SERRKHLFVQ DPQTCKCSCK NTDSRCKARQ LELNERTCRC DKPRR (SEQ ID NO:1). The heparin-binding domain of VEGF165 has the following sequence: ARQENPCGPC SER-RKHLFVQ DPQTCKCSCK NTDSRCKARQ LELNERT-CRC DKPRR (SEQ ID NO:2). The exemplified C-terminal half of the heparin-binding domain of VEGF165 is residues 29-55 of SEQ ID NO:2: CK NTDSRCKARQ LELNERT-CRC DKPRR (SEQ ID NO:3).

A 3-D structure analysis of the 1-55 (111-165 region of VEGF165) heparin binding domain reveals that the 1-29 N-terminal portion of the heparin binding domain has an antiparallel β-sheet structure (18-21, 26-29), and the 29-55 C-terminal portion of the heparin binding domain has a short α-helix (33-38) region packed together with an antiparallel β-sheet structure (42-44, 49-51).

In one aspect of the invention, the VEGF polypeptide that binds to Aβ has a sequence identity of about 70%, 75%, 80%, 85%, 90%, 95%, 96%, 97%, 98% or 99% with SEQ ID NO:1. In another aspect of the invention, the VEGF polypeptide that binds to Aβ has a sequence identity of about 70%, 75%, 80%, 85%, 90%, 95%, 96%, 97%, 98% or 99% with the polypeptide of SEQ ID NO:2. In yet another aspect of the invention, the VEGF polypeptide that binds to Aβ has a sequence identity of about 70%, 75%, 80%, 85%, 90%, 95%, 96%, 97%, 98% or 99% with SEQ ID NO:3. In still another aspect of the invention, the VEGF polypeptide retains the capability of specifically binding to both heparin and Aβ, not necessarily simultaneously. The length of the polypeptide may be about 17 to 100 amino acids long, about 17 to 70 amino acids long, about 17 to 47 amino acids long, about 20 to 45 amino acids long, about 25 to about 40 amino acids long, about 22 to 32 amino acids long, about 25 to 30 amino acids long, or about 27 to 47 amino acids long.

VEGFIAβ Co-Accumulation

VEGF co-accumulates and co-localizes heavily with amyloid plaques in the brain of patients with AD. VEGF binds directly to Aβ peptides with high affinity and specificity. In contrast, VEGF was rarely detected in cortical sections of age-matched subjects. In vitro experiments showed that VEGF bound to Aβs with high affinity and specificity, but not to the reverse peptide, Aβ40-1. Furthermore, the binding of Aβ to VEGF did not affect the binding of VEGF with the receptors on endothelial and tumor cells expressing neuropilin-1 nor the proliferation of endothelial cells induced by VEGF. Conversely, VEGF co-aggregated with Aβ1-40 without apparent effect on Aβ's aggregation rate, and strongly bound to pre-aggregated Aβ VEGF was very slowly released from the co-aggregated Aβ/VEGF complex, but the Aβ/VEGF complex was sensitive to SDS treatment.

It is surprising that VEGF, which is one of the most potent angiogenic factors known, binds directly to Aβ with high affinity, and is heavily accumulated and co-localized with Aβ plaques in the brain of patients with AD. Our results show that VEGF binds to Aβ1-42 and Aβ1-40 much more strongly than other molecules that are known to bind to Aβs (Bohrmann et al., J Biol Chem 1999;274(23):15990-15955; Hamazaki H., J Biol Chem 1995;270(18):10392-10394; Hughes et al., Proc Natl Acad Sci USA 1998;95(6):3275-3280; Strittmatter et al., Proc Natl Acad Sci USA 1993;90(17):8098-8102). VEGF is the strongest binding partner of Aβ ($KD \cong 50$ pM) among the molecules tested, and the affinity between VEGF and Aβ is comparable to that of VEGF for its own receptors, KDR/Flk-1 and Flt-1 (de Vries et al., Science 1992;255(5047):989-991; Terman et al., Biochem Biophys Res Commun 1992;187(3): 1579-1586).

In our studies, Aβs did not affect the cell binding and mitogenic activity of VEGF even though they bound to VEGF with high affinity. The heavy accumulation and co-localization of VEGF with Aβ deposits in the brain of AD patients compared with that of normal elderly subjects could be due to the combination of high expression of VEGF, strong interaction and co-aggregation of VEGF with Aβ, and the very slow release of VEGF from these complexes. This may cause continuous accumulation and co-localization of VEGF to insoluble Aβ deposits in the brain of patients with AD.

Without being bound by theory, it is contemplated that the significance of the accumulation of VEGF with Aβ plaques in AD brain relates to vascular dysfunction in the brain. Most cases of AD are accompanied by cerebrovascular pathology, such as cerebral amyloid angiopathy and endothelial degeneration, suggesting that vascular dysfunction may play a causative role in the neurodegenerative cascade of AD (de la Torre J C. Stroke 2002;33(4):1152-1162; Kalaria R N. Neurobiol Aging 2000;21(2):321-330; Kokmen et al., Neurology 1996;46(1):154-159; Snowdon et al., JAMA 1997;277(10): 813-817; Thomas et al., Nature 1996;380(6570):168-171). Due to its cerebrovascular pathologies, brain cells in AD suffer severely from hypoperfusion of glucose and oxygen. Evidence suggests that cerebral hypoperfusion is one of the major clinical features in the early phases of both sporadic and familial forms of AD, and history and coexistence of ischemic stroke increase the risks for AD (Kalaria R N. Neurobiol Aging 2000;21(2):321-330; Kokmen et al., Neurology 1996;46(1):154-159; Snowdon et al., JAMA 1997;277(10): 813-817).

VEGF is a major regulator of blood vessel function. VEGF is a hypoxia- and hypoglycemia-inducible angiogenic peptide. Furthermore, VEGF and its receptor, induced by hypoxia, enhance angiogenesis and cerebrovascular perfusion, and significantly improve neurological recovery in brain ischemia (Harrigan et al., Neurosurgery 2002;50(3):589-598; Marti et al., Proc Natl Acad Sci USA 1998;95(26):15809-15814; Zhang et al., J Clin Invest 2000;106(7):829-838). Recent studies suggest that VEGF has other activities such as neurotrophic effects under hypoxia and glucose deprivation conditions as well as neuroprotective effects against glutamate toxicity and ischemic peripheral neuropathy (Jin et al., Proc Natl Acad Sci USA 2000;97(18):10242-10247; Matsuzaki et al., FASEB J 2001;15(7):1218-1220; Oosthuyse et al., Nature Genet 2001;28(2):131-138; Schratzberger et al., Nature Med 2000;6(4):405-413; Sondell et al., J Neurosci 1999;19(14):5731-5740), which are implicated in the neuronal pathology of AD.

Since the level of VEGF is increased in the brain of AD patients compared with that of age-matched controls (Kalaria et al., Brain Res Mol Brain Res 1998;62(1):101-105; Tarkowski et al., Neurobiol Aging 2002;23(2):237-243), it is likely that VEGF induced in AD brain may lead to enhanced neovascularization to compensate for the onset of hypoperfusion and inhibit ischemia-induced neuronal death through its direct neuroprotective action on neuronal cells and its angiogenic activity.

However, in AD patients, our results indicate that most of the VEGF expressed during the course of AD may bind to Aβ deposits without turning over. This situation may result in deficiency of soluble VEGF needed for protection of cerebral vessels and neurons against hypoperfusion, which is implicated in the pathology of AD. It is also worthwhile to note that ischemia triggers accumulation and cleavage of the amyloid precursor protein into Aβ and the deposition of Aβ in the brain (Bennett et al., Neurobiol Aging 2000;21(2):207-214; Jendroska et al., Acta Neuropathol (Berl) 1995;90(5):461-466). And in addition to its proposed role in AD pathogenesis (Calhoun et al., Nature 1998;395(6704):755-756; Hardy et al., Science 1992;256(5054):184-185; Hsiao et al., Science 1996;274(5284):99-102; Lewis et al., Science 2001;293 (5534):1487-1491; Schenk et al., Nature 1999;400(6740): 173-177; Sommer B., Curr Opin Pharmacol 2002;2(1):87-92; Thomas et al., Nature 1996;380(6570):168-171), Aβ may act as a molecular sink for VEGF expressed in AD brain, which should aggravate the progression of AD by blocking the angiogenic and neuroprotective activities of VEGF.

VEGF Binding Region of Aβ

Figure 6:
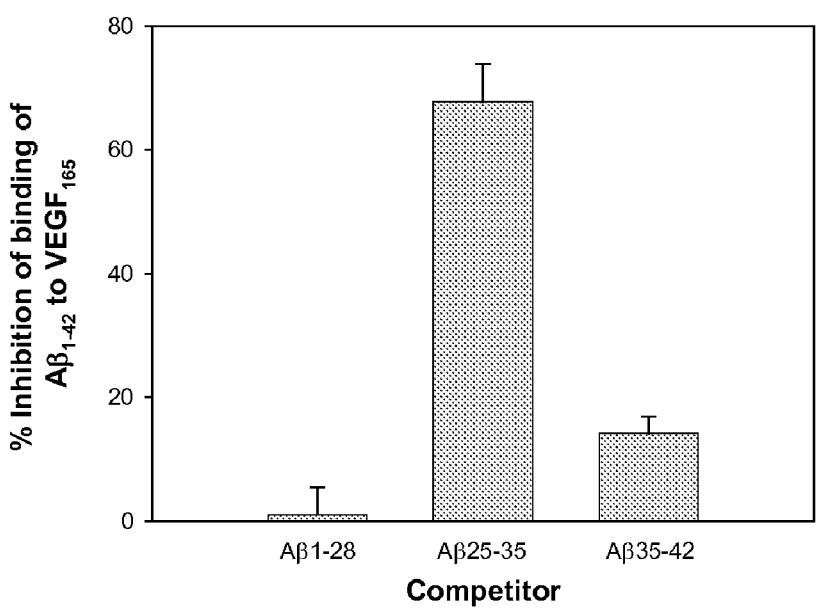
FIG. 6 shows that VEGF binds to residues 25-35 of Aβ. Among various partial fragments of A tested, Aβ25-35 competes with Aβ for its binding to immobilized VEGF165. The result suggests that Aβ25-35 is most likely the binding site for VEGF.

The sequence of Aβ1-42 is: DAEFRHDSGY EVH-HQKLVFF AEDVGSNRGA IIGLMVGGVV IA (SEQ ID NO:4). The 1-28 domain is a hydrophilic domain with high proportion of charged residues (46%); has cross-β structure and forms a fibril. Region 29-42 is richly hydrophobic with a high proportion of β-branched amino acids. Region 25-35 is the biologically active domain for its neurotoxic effect. Applicants discovered that VEGF binds to the 25-35 region of Aβ (FIG. 6).

In one aspect of the invention, the Aβ polypeptide that binds to VEGF has a sequence identity of about 70%, 75%, 80%, 85%, 90%, 95%, 96%, 97%, 98% or 99% with SEQ ID NO:4. In another aspect of the invention, the polypeptide retains the capability of specifically binding to VEGF. The length of the Aβ polypeptide may vary from about 10 to about 42 and may include other sequences attached thereto, which may retain the VEGF binding activity. In particular, the Aβ polypeptide may be from about 10 to about 40 amino acids long, from about 10 to about 35, from about 10 to about 30, from about 10 to 25, from about 10 to 20, from about 10 to 15, or about 10 amino acids long. In another aspect of the invention, the 10 amino acid fragment may be residues 25 to 35 of SEQ ID NO:4.

In one aspect of the invention, the Aβ polypeptide may be used as a trap to immobilize VEGF in areas where there is undesired activity of VEGF, such as excessive angiogenesis, as in rheumatoid arthritis, cancer, atherosclerosis, endometriosis, renal disease and obesity, and the like. The Aβ polypeptide may be full length or longer or shorter or variant or derivatized, so long as the polypeptide has at least a sequence identity of 70% with SEQ ID NO:4, and retains the capability of specifically binding to VEGF.

Inhibitor of VEGF/Aβ Binding

In one embodiment, the invention is directed to screening for a compound such as a polypeptide or chemical compound that inhibits binding of VEGF to Aβ. It is expected that the inhibitor compound will treat persons suffering from diseases that are at least in part caused by the deposit of Aβ and VEGF. If an inhibitor is used, VEGF would not accumulate with Aβ deposit, and thus it will be free to function normally and induce neuroprotective and neurotrophic effects on the diseased area thus treating the disease.

In this regard, in one aspect, the invention is directed to any inhibitor molecule that is capable of interacting with VEGF to block the binding of VEGF to Aβ. In particular, the molecule should interact with the heparin-binding domain of VEGF, and further in particular, the molecule may interact with the C-terminal side of the heparin binding domain. And alternatively, the molecule may bind to Aβ thus disrupting the VEGF/Aβ binding.

One such inhibitor may be VEGF polypeptide, which retains the Aβ binding function but lacks or has decreased level of some or all of the other features associated with VEGF function, such as receptor binding activities or activating signal transduction pathway. Such inhibitor VEGF polypeptide may include the heparin binding domain. In another embodiment, the inhibitor VEGF polypeptide may be β-ABP.

It is understood that the inhibitor compound may impair the interaction between the VEGF polypeptide and Aβ by any number of biochemical or enzymatic inhibition kinetics, such as competitive, non-competitive, or uncompetitive inhibition, so long as the compound impairs the binding of VEGF polypeptide to Aβ.

Thus, in one particular aspect, the invention is directed to using any polymer or monomer compound that is capable of inhibiting binding between VEGF and Aβ. In a specific embodiment, the polymer or monomer has a sugar backbone. The sugar backbone unit may be a glucose or sucrose, or any group that is a six-membered ring with one oxygen atom and the rest carbon atoms. The backbone may have a substituted group, which may be any number of chemical species. Preferably, the substitute group is a phenol or polyphenol, which by way of example, may be formed by reacting with gallic acid. In this regard, tannic acid and pentagalloyl glucose (PGG), which includes both glucose and polyphenol groups have been exemplified herein as being an inhibitor of VEGF/Aβ binding. Furthermore, it is contemplated that the inhibitor be a catechin or a catechin phenol compound, which includes but is not limited to epicatechin (EC), epicatechin gallate (ECG), epigallocatechin (EGC), or epigallocatechin gallate (EGCG). See Jung et al., Int J Exp Path 2001;82:309-316 (incorporated by reference in its entirety) for a description of these compounds and their activities.

It is also understood that several different variations may be made to the sugar backbone. Thus, in one particular embodiment of the invention, molecules that mimic heparin or PGG are within the framework of the invention, so long as these mimics or analogs inhibit the binding between VEGF and Aβ. In this regard, it is understood that analogs and mimics of heparin, PGG, EGCG, and tannic acid are included in the invention. Further, such inhibitors may include various types of glycosaminoglycan chains, such as hyaluronic acid, chondroitin sulfate, keratan sulfate, dermatan sulfate and so on, which may be molecules that are related to heparin.

Some of the heparin related molecules may include without limitation, hyaluronic acid, wherein the D-Glucuronic acid and N-Acetyl-D-glucosamine unit may be repeated up to about 50,000 units; chondroitin sulfate, wherein the D-Glucuronic acid and N-Acetyl-D-galactosamine unit may be repeated up to about 250,000 units; dermatan sulfate, wherein the L-lduronic acid and N-Acetyl-D-galactosamine unit may be repeated up to about 250,000 units, and at least one hydroxyl group may be substituted with a sulfate group; heparin or haparan sulfate, wherein the D-Glucuronic or L-lduronic acid and N-Acetyl- or N-sulfo-D-glucosamine unit may be repeated about 15 to 30 units, wherein in certain instances, having at least one sulfate group substituted for a hydroxyl group is preferred; keratan sulfate, wherein the D-Galactose and N-Acetyl-D-glucosamine unit may be repeated about 20 to 40 times, wherein at least one hydroxy group is substituted with a sulfate group.

In another embodiment of the invention, extracts of natural foods or 'functional foods' are contemplated as comprising inhibitors of VEGF/Aβ complex. Tea catechins is but one example of such category of inhibitors. In addition to catechins, other polyphenols that are major ingredients of functional foods include, but are not limited to flavonoids, resveratrol, and quercetin.

The chemical structure of heparin is shown below.

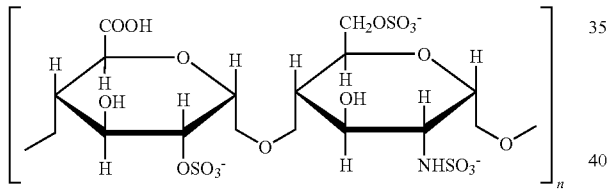

The chemical structure of PGG is shown below.

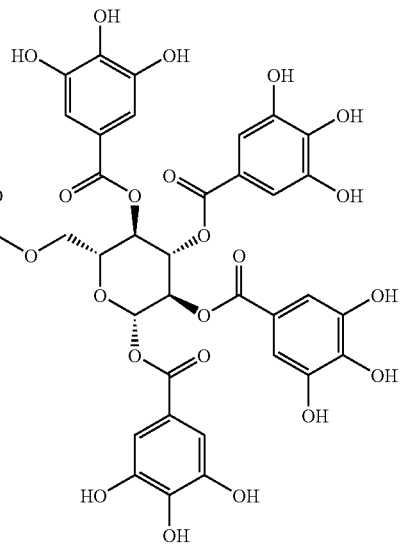

The chemical structure of EGCG is shown below.

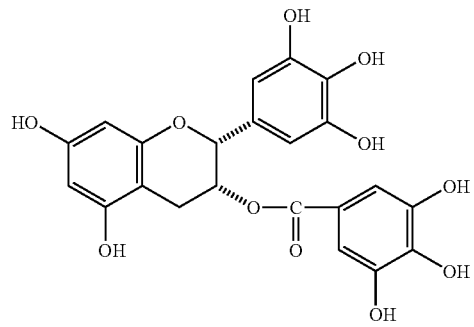

The chemical structure of tannic acid is shown below.

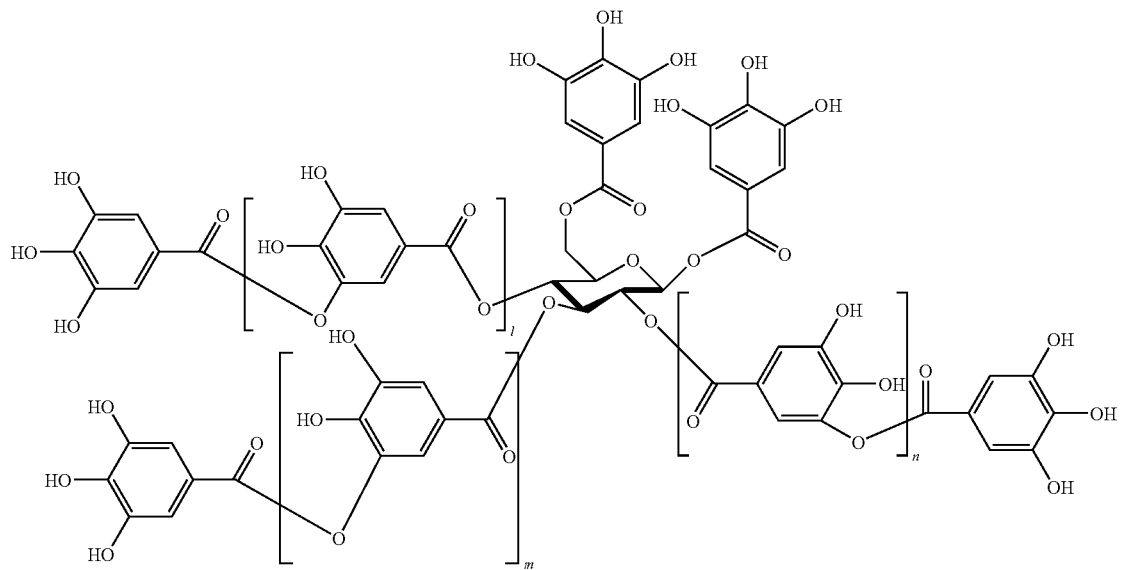

$l + m + n = 0, 1, 2, 3, 4, 5, 6, 7$

Nucleic Acid Encoding Polypeptide that Binds to Aβ or VEGF

By "isolated" polynucleotide sequence, it is intended to encompass a nucleic acid molecule, DNA or RNA, which has been removed from its native environment. This includes segments of DNA encoding VEGF polypeptide or Aβ polypeptide of the present invention, and may further comprise heterologous sequences such as vector sequences or other foreign DNA. For example, recombinant DNA molecules contained in a vector are considered isolated for the purposes of the present invention, which may be partially or substantially purified.

In addition, isolated nucleic acid molecules of the invention include DNA molecules, which comprise a sequence substantially different from those described above but which, either due to the degeneracy of the genetic code or other variability, still encode VEGF polypeptide or Aβ polypeptide and their peptides. Thus, it would be routine for one skilled in the art to generate the variants described above, for instance, to optimize codon expression or general function for a particular host.

In another aspect, the invention provides an isolated nucleic acid molecule comprising a polynucleotide which hybridizes under stringent hybridization conditions to a portion of a polynucleotide in a nucleic acid molecule of the invention described above. Hybridizing polynucleotides are useful as diagnostic probes and primers as discussed above. Portions of a polynucleotide which hybridize to the VEGF polypeptide encoding sequence as exemplified and set forth as SEQ ID NOS:1-3, which can be used as probes and primers, may be precisely specified by 5' and 3' base positions or by size in nucleotide bases as described above or precisely excluded in the same manner. Similarly, portions of a polynucleotide which hybridize to the Aβ polypeptide exemplified and set forth as SEQ ID NO:4 may be used as probes and primers as well. Preferred hybridizing polynucleotides of the present invention are those that, when labeled and used in a hybridization assay known in the art (e.g. Southern and Northern blot analysis), display the greatest signal strength regardless of other heterologous sequences present in equimolar amounts.

Variant and Mutant Polynucleotides

The present invention further relates to variants of the nucleic acid molecules which encode portions, analogs or derivatives of VEGF polypeptide or Aβ polypeptide. Variants may occur naturally, such as a natural allelic variant. By an "allelic variant" is intended one of several alternate forms of a gene occupying a given locus on a chromosome of an organism. Non-naturally occurring variants may be produced using art-known mutagenesis techniques.

Such nucleic acid variants include those produced by nucleotide substitutions, deletions, or additions. The substitutions, deletions, or additions may involve one or more nucleotides. Alterations in the amino acid sequence may produce conservative or non-conservative amino acid substitutions, deletions or additions. Especially preferred among these are silent substitutions, additions and deletions, which do not alter the properties and activities of the polypeptides of the present invention or portions thereof. Also preferred in this regard are conservative substitutions.

The present application is directed to nucleic acid molecules encoding a polypeptide that is at least 70%, 75%, 80%, 85%, 90%, 95%, 96%, 97%, 98% or 99% identical to the polypeptide of SEQ ID NO:3 or SEQ ID NO:4, with the understanding that the polypeptides retain the function of specifically binding to Aβ or VEGF, respectively.

The invention allows for the use of sequences in expression vectors, as well as to transfect host cells and cell lines, be these prokaryotic or eukaryotic cells. The invention also allows for purification of the polypeptides expressed from the expression vector. The expression vector may contain various molecular tags for easy purification. Subsequently obtained expression construct may be transformed into any host cell of choice. Cell lysates from the host cell is isolated by established methods well known in the field. GFP- or GST-containing expression vector may be used to localize VEGF polypeptide or Aβ polypeptide in the host cell. The expression vector may contain an inducible or constitutive promoter.

Variant and Mutant Polypeptides

To improve or alter the characteristics of VEGF polypeptide or Aβ polypeptide of the present invention, amino acid engineering may be employed. Recombinant DNA technology known to those skilled in the art can be used to create novel mutant polypeptides including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions.

Of special interest are substitutions of charged amino acids with other charged or neutral amino acids which may produce proteins with highly desirable improved characteristics, such as less aggregation of the produced polypeptides. Aggregation may not only reduce activity but may also be problematic when preparing pharmaceutical formulations, because aggregates can be immunogenic.

Antibodies

In one embodiment, the present invention is directed to detecting Aβ formation using a variety of detection methods. One way to detect binding of VEGF polypeptide to Aβ is to label the VEGF polypeptide directly and assay for its binding using labeling and separation techniques that are routine to a person of skill in the art. Other methods include using a labeled ligand that specifically binds to either the VEGF polypeptide, Aβ or VEGF polypeptide/Aβ complex. Such a ligand may be an antibody.

Purified VEGF polypeptide, Aβ or VEGF polypeptide/Aβ complex can be used to produce monoclonal or polyclonal antibody. Fragments of VEGF polypeptide also can be used to produce monoclonal or polyclonal antibody. Subsequently obtained monoclonal or polyclonal antibody can be used to determine the binding of VEGF polypeptide to Aβ and the formation of a VEGF polypeptide, Aβ or VEGF polypeptide/Aβ complex in various samples including cells, tissues, and body fluids such as but not limited to serum, plasma, and urine. VEGF polypeptide, Aβ or VEGF polypeptide/Aβ complex may be assayed using a variety of molecular biological methods, which include but are not limited to in situ hybridization, immunoprecipitation, immunofluorescence staining, Western blot analysis and so on. One can carry out ELISA by using monoclonal antibody against VEGF polypeptide, Aβ or VEGF polypeptide/Aβ _complex, to determine the amount of Aβ in the brain tissue or other parts of the body, including body fluids of human subjects believed to have an indicated disorder in which Aβ is aggregated and is accumulated and form amyloid plaques.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention, which they recognize or specifically bind. The epitope(s) or polypeptide portion(s) may be specified as described herein, e.g., by N-terminal and C-terminal positions, by size in contiguous amino acid residues.

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of VEGF polypeptide, Aβ or VEGF polypeptide/Aβ complex of the present invention in biological samples.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with a VEGF polypeptide, Aβ or VEGF polypeptide/Aβ complex or a cell expressing such entity. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention or its complex with its binding partner. Ascites fluid, which generally contains high levels of antibodies, can be generated by immunizing mice with positive hybridoma clones.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Assays for Antibody Binding

The antibodies of the invention may be assayed for immunospecific binding by any method known in the art. The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below but are not intended by way of limitation.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, which may include a sample comprising VEGF polypeptide, Aβ or VEGF polypeptide/Aβ, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added simultaneously or following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Diagnostic Assay

The invention also provides diagnostic methods for detecting the presence of Aβ in a biological sample. This may be assayed either directly (e.g., by assaying polypeptide levels using antibodies elicited in response to VEGF polypeptide or fragments thereof) or indirectly (e.g., by assaying for antibodies having specificity for VEGF polypeptide or fragments thereof).

Where diagnosis of a diseased state has already been made, the present invention is useful for monitoring progression or regression of the disease state by measuring the amount of Aβ/VEGF complex present in a patient or whereby patients exhibiting enhanced Aβ production will experience a worse clinical outcome relative to patients producing Aβ at a lower level.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography, as well as, electron paramagnetic resonance (EPR) and nuclear magnetic resonance (NMR).

In a specific embodiment, a molecule such as a polypeptide that specifically binds to Aβ is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

In one aspect, the in vivo diagnosis may be made by using a label that is detectable by the above described methods or some other mechanism, which is non-toxic to the subject, injecting the labeled polypeptide into a subject such that the polypeptide travels and binds to its binding target, such as a Aβ aggregated region, whereby the presence of the target mass, such as Aβ or Aβ aggregate is detected.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine (125I, 121I), carbon (14C), sulphur (35S), tritium (3H), indium (112In), and technetium (99mTc), and fluorescent labels, such as fluorescein and rhodamine, and biotin.

Further suitable labels for the VEGF polypeptide-, Aβ- or VEGF polypeptide/Aβ complex-specific antibodies of the present invention are provided below. Examples of suitable enzyme labels include malate dehydrogenase, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include 3H, 111In, 125I, 131I, 32P, 35S, 14C, 51Cr, 57To, 58Co, 59Fe, 75Se, 152Eu, 90Y, 67Cu, 217Ci, 211At, 212Pb, 47Sc, 109Pd, etc. 111In is preferred isotope where in vivo imaging is used since its avoids the problem of dehalogenation of the 125I or 131I-labeled polypeptide by the liver. In addition, this radionucleotide has a more favorable gamma emission energy for imaging. For example, 111In coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include 157Gd, 55Mn, 162Dy, 52Tr, and 56Fe.

Examples of suitable fluorescent labels include an 152Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Deuterium may also be used. Other contrasting agents also exist for EPR, PET or other imaging mechanisms, which are known to persons of skill in the art.

Typical techniques for binding the above-described labels to polypeptides are provided by Kennedy et al. (1976) Clin. Chim. Acta 70:1-31, and Schurs et al. (1977) Clin. Chim. Acta 81:1-40. Coupling techniques include the glutaraldehyde method, the periodate method, the dimaleimide method, the m-maleimidobenzyl-N-hydroxy-succinimide ester method, all of which methods are incorporated by reference herein.

The polypeptides and antibodies of the present invention, including fragments thereof, may be used to detect VEGF polypeptide, Aβ or VEGF polypeptide/Aβ complex using biochip and biosensor technology. Biochip and biosensors of the present invention may comprise the polypeptides of the present invention to detect antibodies, which specifically recognize VEGF polypeptide/Aβ complex. Bio chip and biosensors of the present invention may also comprise antibodies which specifically recognize the polypeptides of the present invention to detect VEGF polypeptide/Aβ complex.

Kit

The invention also includes a kit for analyzing samples for the presence of VEGF polypeptide/Aβ complex in a biological sample. In a general embodiment, the kit comprises ligand which binds specifically to VEGF polypeptide, Aβ or VEGF polypeptide/Aβ complex, which may be preferably a purified antibody to VEGF polypeptide, or VEGF polypeptide/Aβ complex, in one or more containers. In a specific embodiment, the kit of the present invention contains a substantially isolated polypeptide comprising an epitope which is specifically immunoreactive with an antibody included in the kit. Preferably, the kit of the present invention further comprises a control antibody which does not react with the polypeptide of interest. The kit further comprises instructions and labels on its use.

In another specific embodiment, the kit of the present invention contains a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate), and instructions and labels on its use.

The kit may also contain labeled VEGF polypeptide with instructions for its use as a Aβ detector.

High Affinity Trap for Aβ and VEGF

Ligand trap, which blocks ligand activity, functions as selective high affinity antagonist of its cognate ligand by sequestering the ligand and thus rendering it unavailable to interact with its native counterpart such as a receptor or co-aggregation assembly. Some of the details on making such ligand traps may be found in U.S. Pat. No. 6,472,179, which is incorporated by reference herein in its entirety.

The ligand trap may comprise VEGF polypeptide associated with other molecules, including but not limited to, polypeptides such as a heteromeric immunoglobulin heavy/light chain receptor, to form a trap that will bind or sequester Aβ, preferably free-floating Aβ. Conversely, the ligand trap may comprise Aβ polypeptide associated with other molecules, including but not limited to, polypeptides such as a heteromeric immunoglobulin heavy/light chain receptor, to form a trap that will bind or sequester VEGF. The heteromeric ligand trap may be comprised of interdisulfide linked proteins if a chemically bonded trap is desired. Or, such ligand trap may be formed by using recombinant fusion protein.

For example, in one embodiment, a high affinity trap for a ligand such as VEGF or Aβ may be made in which one of skill in the art would create fusion nucleic acid comprising a nucleotide sequence encoding a first polypeptide component comprising the amino acid sequence of a ligand binding domain; and at least one other nucleotide sequence encoding a polypeptide component comprising the amino acid sequence of a multimerizing component (for example, an Fc domain of IgG) to create a high affinity trap for the ligand. The fusion construct may be comprised of DNA encoding at least one ligand binding domain polypeptide and at least one polypeptide that encodes a multimerizer. Or, the multimerizer and the ligand binding domain may be encoded and expressed in different DNA constructs. However, it is to be understood that the multimerizing component is not limited to a polypeptide, but may include any molecule which is capable of on the one hand binding to the ligand and on the other hand, associating with other multimerizing components so that a ligand trap is formed.

The ligand binding trap may be soluble or it may be associated with a solid surface. Moreover, the ligand binding trap may be tested for its ability to bind either VEGF or Aβ in a variety of different assays. For example, the dissociation rate of VEGF or Aβ bound to the ligand trap may be measured in parallel with the dissociation rate of VEGF or Aβ from the anti-VEGF or anti-Aβ monoclonal neutralizing antibody. A pre-determined amount of the labeled ligand may be preincubated with a monoclonal antibody or the ligand trap for about 20 hours. An excess of unlabeled ligand may be added. Periodically, aliquots of the reaction may be removed and the ligand trap may be precipitated with Protein G-Sepharose, and the number of counts of label that remain bound may be determined.

Gene Therapy

In a specific embodiment, nucleic acids comprising sequences encoding the VEGF polypeptide or Aβ polypeptide are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a VEGF polypeptide or a Aβ polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

In one embodiment, the present invention relates to treatment for various diseases that are characterized by the formation of Aβ aggregates or amyloid plaque. In this way, the inventive therapeutic compound may be administered to human patients who are either suffering from, or prone to suffer from the disease by providing compounds that inhibit the binding of VEGF to Aβ. In particular, the disease is associated with dementia, chronic neurodegenerative disorder of the brain, loss of nerve cell, particularly in the hippocampus and cerebral cortex, reduced neurotransmitters, cerebrovascular degeneration, and/or loss of cognitive ability. Further in particular, the present invention is directed to a treatment for Alzheimer's disease.

In another embodiment, the present invention relates to treating various diseases that are characterized by excessive angiogenesis, which include but are not limited to, cancer, atherosclerosis, rheumatoid arthritis, endometriosis, renal disease or obesity. Aβ peptide in various forms, including a Aβ ligand trap, may be administered to patients suffering from these diseases so that VEGF, which is a major causative agent in angiogenesis, is bound and inactivated.

The formulation of therapeutic compounds is generally known in the art and reference can conveniently be made to Remington's Pharmaceutical Sciences, 17th ed., Mack Publishing Co., Easton, Pa., USA. For example, from about 0.05 g to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

Affection of VEGF on Cytotoxicity of Aβ

In the present invention, it is suggested the possibility that the binding of VEGF affects cytotoxicity of Aβ, based on the fact that VEGF binds to Aβ at the amino acid region from about position 25 to about position 35 in Aβ, which plays an important role in cytotoxicity of Aβ. In the present invention, it is found that VEGF concentration-dependently inhibits the cytotoxicity of Aβ.

Affection of VEGF on Aggregation of Aβ

Based on the fact that the cytotoxicity of Aβ is proportional to the degree of aggregation of Aβ, and that the amino acid region from about position 25 to about position 35 in Aβ, to which VEGF binds, is also important in aggregation of Aβ, In the present invention, it is found that VEGF concentration-dependently inhibits the aggregation of Aβ.

Affection of VEGF on the Activity of Aβ to Generate Reactive Oxygen Species

In the present invention, it is found that VEGF inhibits the generation of the reactive oxygen species by Aβ. Since the mechanism of the cytotoxicity of Aβ appears to act mostly through generation of reactive oxygen species, such inhibitory effect of VEGF is importance in treating the conditions associated with the generation of the reactive oxygen species Aβ as well as with the cytotoxicity of Aβ.

Inhibitor of VEGF-Aβ Binding

The present invention provides a novel inhibitor of the binding between VEGF and Aβ, triamterene. Triamterene is useful inhibitor of VEGF-Aβ binding, since it exhibits the inhibitory effect on the VEGF-Aβ binding only, with no effect on aggregation of Aβ and VEGF-VEGF receptor binding.

Further, triamterene resolves the problem of VEGF deficiency which is caused by the co-deposition of VEGF and Aβ, by inducing VEGF trapping into Aβ.

EXAMPLES

Example 1

Histology and Immunocytochemistry

Formalin-fixed cerebral cortex autopsy tissues were obtained from the Boston University Alzheimer's Disease Center. The frozen brains were sectioned at a thickness of 30 (m. The sections were mounted on gelatin-coated glass slides, post-fixed with 3.5% paraformaldehyde for 30 min, and then pre-incubated with 0.3% $H_2O_2$ for 15 min. For immunohistochemistry, the sections were treated with 0.25% Triton X-100, incubated with 10% horse serum for 1 hr, and reacted with either mouse monoclonal antibody against Aβ (ZYMED, South San Francisco, USA) or goat polyclonal antibody against human VEGF (R&D Systems Inc., Minneapolis, USA) for 12-16 hr. The sections were then reacted with Texas red-conjugated anti-mouse IgG (Vector Laboratories, Burlingame, USA) or biotinylated rabbit anti-goat IgG (Vector Laboratories). The latter was reacted with fluorescein-conjugated streptavidin (Vector Laboratories). For Congo Red staining, the immunolabeled sections were incubated for 20 min in saturated alcoholic sodium chloride solution (4% (w/v) NaCl in 80% EtOH) that was alkalized with 2.5 mM of NaOH before use and then 0.2% Congo Red (Sigma-Aldrich, St. Louis, USA) was added. After 20 min, the sections were rinsed with absolute ethanol and mounted with VECTASHIELD Mounting Medium (Vector Laboratories).

Example 2

Binding Assay

Binding of known Aβ-binding proteins and VEGF to Aβ peptides were determined by surface plasmon resonance spectroscopy. $A\beta_{1-40}$, $A\beta_{1-42}$, and $A\beta_{40-1}$ (BACHEM, Bubendorf, Switzerland) were immobilized on a CM5 sensor chip (BIAcore AB, Uppsala, Sweden) with an amine coupling kit. Alpha2-macroglobulin, alpha1-antichymotrypsin, serum amyloid P component, apolipoprotein E4, and $VEGF_{165}$ (100 nM) were allowed to bind to the immobilized Aβ at a flow rate of 10 μl/min and sensorgrams were recorded in real time. For determination of binding affinity, microtiter wells were coated with 0.5 μM of Aβ peptides (100 μl), excess sites were blocked with binding buffer (0.1% BSA in M199/25 mM HEPES/NaOH, pH 7.4), and binding was assayed by adding 50 pM of $^{125}$I-VEGF (Amersham Pharmacia Biotech, Buckinghamshire, England) alone or in the presence of varying concentrations of unlabeled VEGF.

Example 3

Co-aggregation Assay

The aggregation of $A\beta_{1-40}$ was determined as described with some modifications (Chang et al., Brain Res Brain Res Protoc 2000;6(1-2):6-12). After a two day incubation of $A\beta_{1-40}$ (100 μM) with FITC-conjugated $A\beta_{1-40}$ (1 μM) in 50 mM MES, pH 5.8, at 37° C., the mixture was centrifuged, and fluorescence in the pellet was measured. For co-aggregation of VEGF with Aβ, 100 μM of $A\beta_{1-40}$ or $A\beta_{40-1}$ was mixed with $^{125}$I-$VEGF_{165}$ (1 nM) and incubated at 37° C. for 2 days. Then the mixtures were centrifuged and radioactivity in pellet was determined in a gamma-counter. To investigate the effect of VEGF on the aggregation rate of Aβ, mixtures of $A\beta_{1-40}$ alone (50 μM of $A\beta_{1-40}$ and 1 μM of FITC- $A\beta_{1-40}$) or $A\beta_{1-40}$ with 1 μM of VEGF were incubated at 37° C., and the extent of aggregation was determined by measuring fluorescence in the pellet after centrifugation. For binding of VEGF to pre-aggregated $A\beta_{1-40}$, 50 μM of fresh Aβ or Aβ preincubated for 2 days was mixed with $^{125}$I-VEGF (1 nM) and immediately centrifuged. The radioactivity in the pellet was determined.

Example 4

Dissociation Assay

For dissociation of VEGF from the Aβ/VEGF co-aggregate, the pellet obtained in co-aggregation assay was resuspended in 50 mM MES, pH 5.8, incubated for different periods of time and centrifuged. The radioactivity in the supernate was determined. To investigate the sensitivity of Aβ/VEGF complex to SDS treatment, non-reducing SDS-PAGE sample dye wad added to either $^{125}$I-$VEGF_{165}$ or the pellet obtained in co-aggregation assay and the mixtures were boiled for 10 min. The mixtures were separated by SDS-PAGE (10%) and autoradiographed.

Example 5

Results

Example 5.1

VEGF is co-localized with amyloid plaques in the brain of patients with AD. We examined if the expression pattern of VEGF was altered in the temporal cortex of AD patients. We observed enhanced VEGF immunoreactivity in the brain of AD patients compared to that of elderly controls (FIGS. 1A and C). Unexpectedly, heavy accumulation of VEGF was observed in congophilic plaques in the cortical areas of AD patients (FIGS. 1A and B). VEGF immunoreactivity and amyloid plaques were rarely detected in cortical sections of age-matched subjects (FIGS. 1C and D). Double immunocytochemistry revealed that VEGF was colocalized with Aβ in the neuritic and diffuse plaques of AD patients (FIGS. 1E-1G). Similar results were obtained from all of the AD brain samples we have examined (seven patients).

Example 5.2

Figure 2A:
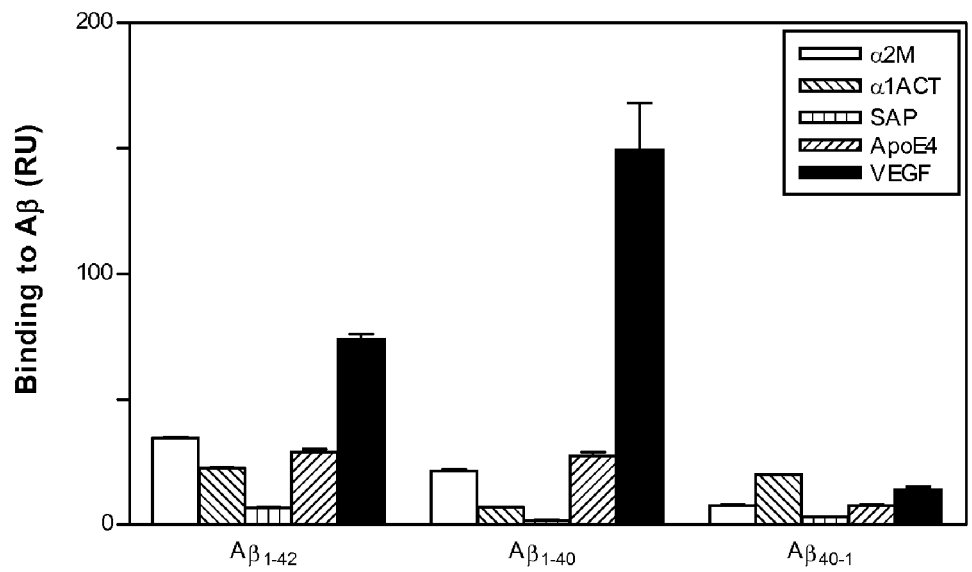
FIGS. 2A-2C show specific binding of VEGF to Aβs. A and B, Plasmon resonance analysis of interaction of known Aβ-binding proteins and VEGF with Aβ peptides immobilized on a CM5 sensorchip. RU, resonance units. A, Binding of known Aβ-binding proteins and VEGF to Aβ peptides. α2M, alpha2-macroglobulin; α1ACT, alpha1-antichymotrypsin; SAP, serum amyloid P component; ApoE4, apolipoprotein E4. B, Sensorgrams of varying concentrations of VEGF applied to immobilized Aβ1-40. Similar binding sensorgrams were obtained with Aβ1-42 (data not shown). C, Inhibition of 125I-VEGF binding to immobilized Aβ1-40 by unlabelled VEGF. A similar inhibition pattern was obtained with immobilized Aβ1-42 (data not shown). All values expressed as mean±SEM.
Figure 2B:
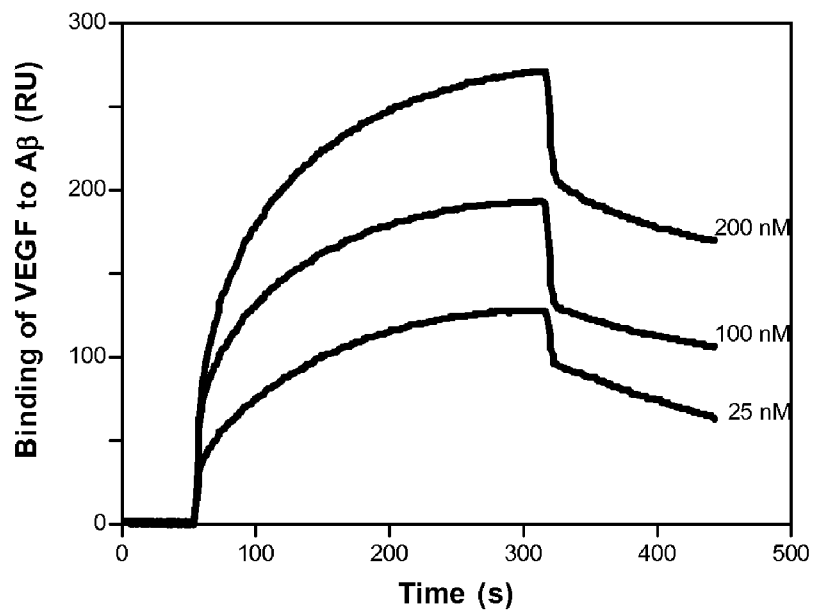

VEGF binds to Aβ peptides with high affinity and specificity. We investigated if Aβ and VEGF interact with each other with specificity and high affinity. We immobilized $A\beta_{1-42}$, $A\beta_{1-40}$, and $A\beta_{40-1}$ on a BIAcore CM5 sensor chip and investigated the binding of VEGF and other molecules to Aβ peptides by surface plasmon resonance spectroscopy (FIG. 2A and B). The results show that VEGF bound to $A\beta_{1-42}$ and $A\beta_{1-40}$ much more strongly than other molecules that are known to bind to Aβs (Bohrmann et al., J Biol Chem 1999; 274(23):15990-15955; Hamazaki H., J Biol Chem 1995;270 (18):10392-10394; Hughes et al., Proc Natl Acad Sci USA 1998;95(6):3275-3280; Strittmatter et al., Proc Natl Acad Sci USA 1993;90(17):8098-8102) such as alpha2-macroglobulin, alpha1-antichymotrypsin, serum amyloid P component, and apolipoprotein E4. ELISA analysis with biotinylated $A\beta_{1-40}$ showed similar results as those obtained by surface plasmon resonance spectroscopy (data not shown).

Figure 2C:
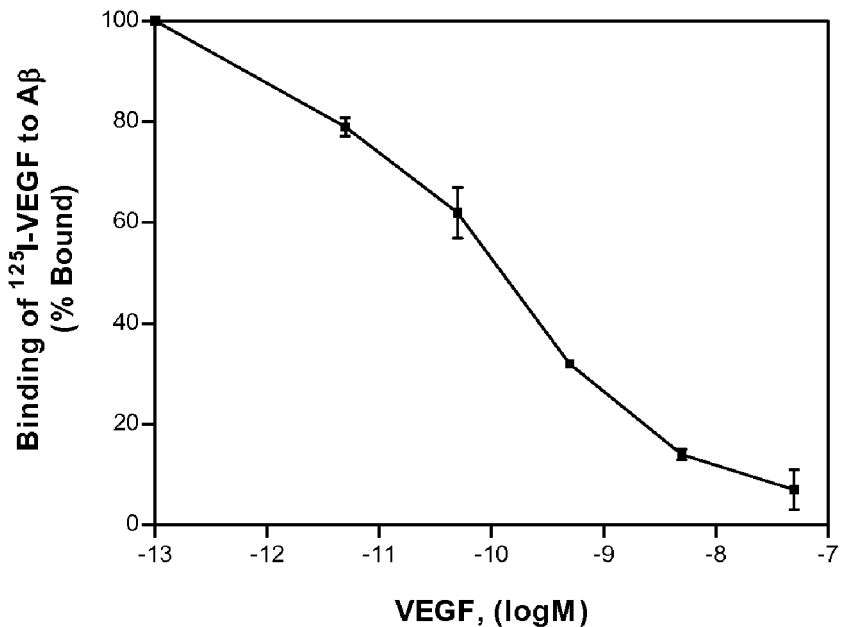

VEGF did not bind to $A\beta_{40-1}$, the peptide with reverse order of the amino acid sequence of $A\beta_{1-40}$. We determined binding affinity between Aβ and VEGF by analyzing binding of radiolabeled VEGF to immobilized Aβ peptides in the presence of increasing concentrations of non-labeled VEGF (FIG. 2C). In this assay, the dissociation constant of approximately 50 pM was obtained for $A\beta_{1-40}$ ($K_D=IC_{50}-[^{125}I-VEGF]$) (DeBlasi et al., Trends Pharmacol Sci 1989;10(6): 227-229). $A\beta_{1-42}$ showed similar binding affinity for VEGF (data not shown). These results suggest that VEGF directly binds with Aβ peptides with specificity and high affinity.

Example 5.3

Aβ peptides have little effect on the cell binding and mitogenic activity of VEGF. We next investigated the effect of Aβ peptides on the cell binding and mitogenic activity of VEGF. Neither $A\beta_{1-40}$ nor $A\beta_{1-42}$, even at a high concentration (1 μM), affected the binding of VEGF with the receptors on endothelial cells or the proliferation of endothelial cells induced by VEGF (data not shown). Recent studies show that VEGF interacts with neuropilin-1 that is expressed on neuronal and endothelial cells and in some tumors (Soker et al., Cell 1998;92(6):735-745). Neither did $A\beta_{1-40}$ nor $A\beta_{1-42}$ affect the binding of VEGF to MDA-MB-231 tumor cells that express neuropilin-1 (data not shown). Taken together, $A\beta$ peptides do not seem to affect the cell binding and mitogenic activity of VEGF even though they bind to VEGF with high affinity.

Example 5.4

Figure 3:
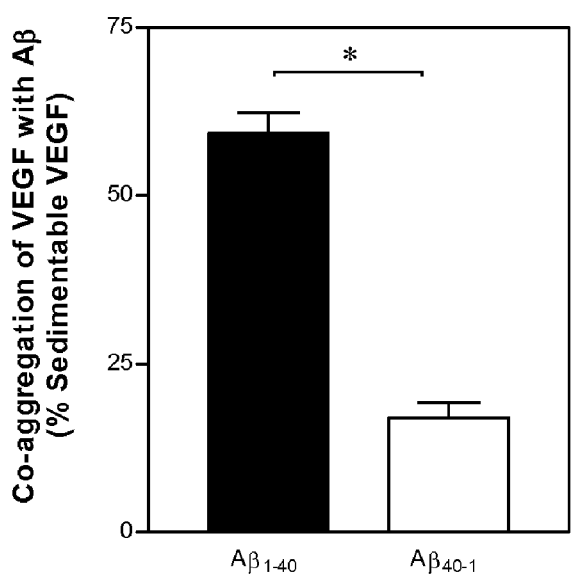
FIGS. 3A-3C show co-aggregation of VEGF with Aβ. A, VEGF is co-aggregated with Aβ1-40 but not with Aβ40-1. Approximately the same proportion of input Aβ1-40 and labeled VEGF appeared in the pellet after centrifugation. *, P=0.0076. B, VEGF has no effect on the aggregation rate of Aβ. Sedimentable Aβ from the incubation of Aβ1-40 alone (■, solid line) and Aβ1-40 with VEGF (▲, dotted line) were shown after various incubation time points. C, Efficient co-precipitatation of VEGF with pre-aggregated, but not with freshly dissolved Aβ1-40. The result shows the binding of VEGF to pre-aggregated Aβ. **, P<0.0001. All values expressed as mean±SEM.
Figure 3B:
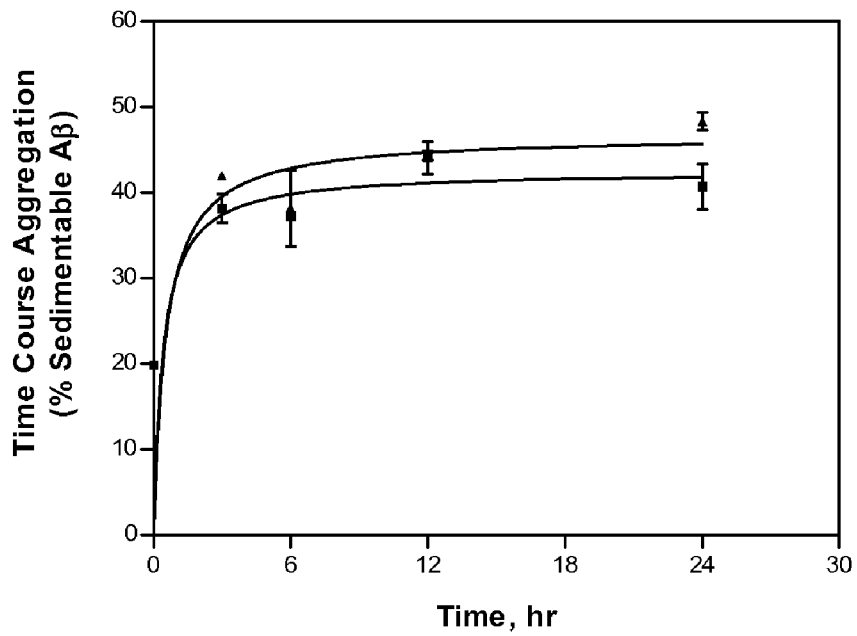
Figure 3C:
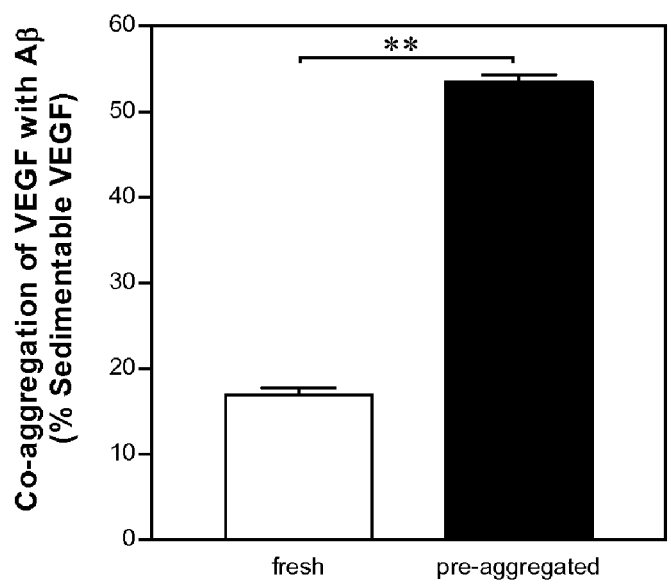
Figure 4A:
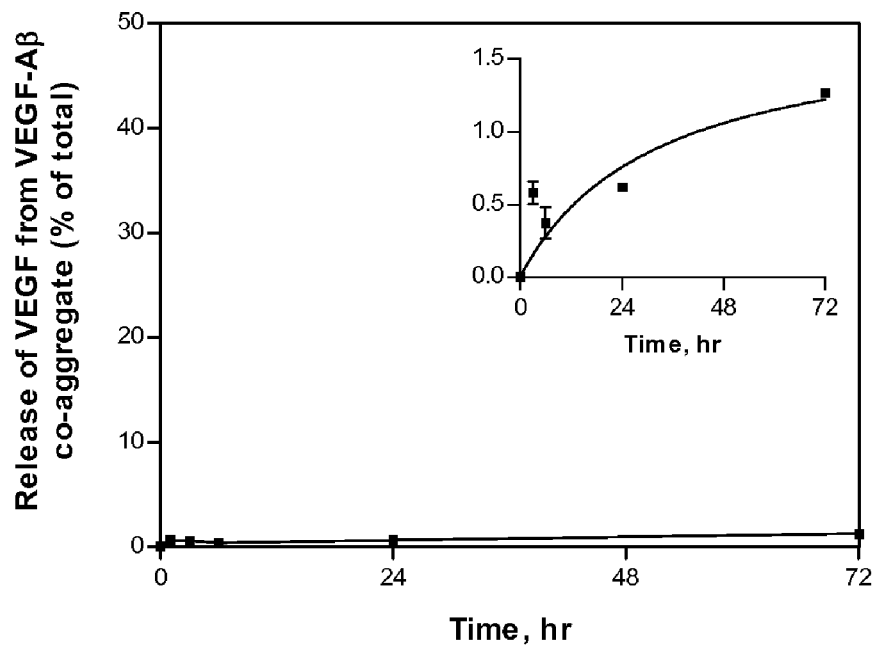
FIGS. 4A-4B show slow release of VEGF from Aβ/VEGF co-aggregate. A, VEGF slowly dissociates from the Aβ/VEGF co-aggregate. Inset, note that less than 1.5% of VEGF is released from co-aggregate after 3 days. All values expressed as mean±SEM. B, Aβ/VEGF complex is sensitive to SDS treatment. The autoradiogram is shown after SDS-PAGE of the pellet obtained in A under non-reduced conditions. Lane 1: 125I-VEGF alone. Lane 2: Aβ/125I-VEGF complex. Numbers on the left indicate positions of size markers. Note there is no additional band in the Aβ/VEGF complex compared with that of VEGF alone.
Figure 4B:
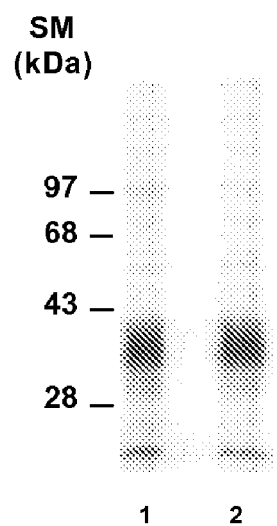

VEGF is co-aggregated with $A\beta$, strongly binds to pre-aggregated $A\beta$, and is very slowly released from the co-aggregated complex. Since VEGF accumulates in $A\beta$ plaques in AD brain and strongly interacts with $A\beta$ peptides, we examined the mechanism whereby VEGF is co-aggregated with $A\beta$. When we incubated $A\beta$ alone for 2 days, approximately 60% of the $A\beta$ appeared in the pellet after centrifugation (data not shown). About the same proportion of VEGF also appeared in the pellet when $^{125}$I-VEGF and $A\beta_{1-40}$ were incubated together in solution (FIG. 3A). However, the presence of the reverse peptide, $A\beta_{40-1}$, did not cause extensive sedimentation of VEGF (P=0.0076). Time course experiments showed that VEGF (1 μM) had no significant influence on the aggregation of 50 μM and 100 μM of $A\beta_{1-40}$ (FIG. 3B and data not shown). When VEGF was mixed with fresh or pre-aggregated $A\beta$ and immediately centrifuged, VEGF bound to pre-aggregated $A\beta$ and these complexes could be pelleted by centrifugation (FIG. 3C). We next investigated the dissociation rate of VEGF from the $A\beta$/VEGF complex. After 3 days, less than 1.5% of the VEGF was released from the complex (FIG. 4A). However, the $A\beta$/VEGF complex is sensitive to SDS treatment (FIG. 4B). These results clearly indicate that VEGF is co-aggregated with $A\beta$ without any apparent effect on the rate of $A\beta$ aggregation, strongly binds to pre-aggregated $A\beta$, and is very slowly released from the co-aggregated $A\beta$/VEGF complex.

Example 6

Determination of $A\beta$ Binding Region in VEGF

For determination of $A\beta$ binding region in VEGF, we fused whole VEGF, heparin-binding domain, and partial domain of heparin-binding domain with Glutathine-S-transferase (GST) as previously described (Soker et al., J Biol Chem 1996;272(50):31582-31588). The purified proteins were analyzed with 12% SDS-polyacrylmide gel electrophoresis. GST and GST-fusion proteins were immobilized on the microtiter wells at concentration of 200 nM, whereas VEGF was immobilized at 100 nM, because a VEGF dimer has two heparin-binding domains. After blocking nonspecific binding sites with 3% BSA/PBS, 200 nM of $A\beta$ was added to each well and allowed to bind to immobilized proteins. Unbound $A\beta$ was removed and the bound $A\beta$ was determined with rabbit anti-$A\beta$ antibody followed by anti-rabbit antibody conjugated with horse radish peroxidase. See FIG. 5 for the results.

Example 7

Determination of VEGF Binding Region in $A\beta$

VEGF binding region in $A\beta$ was determined by two methods. VEGF was immobilized on microtiter wells at a concentration of 100 nM and nonspecific sites were blocked with 3% BSA/PBS. $A\beta_{1-42}$ (50 nM) alone or in the presence of 30 μM of mutant $A\beta$s was added to the well and allowed to bind to the immobilized VEGF. After removing unbound $A\beta$, the bound $A\beta$ was determined by binding of rabbit anti-$A\beta$ antibody followed by anti-rabbit antibody conjugated with horse radish peroxidase. Alternatively, biotinylated $A\beta_{1-42}$ (50 nM), instead of $A\beta$, was added alone or in the presence of 50 μM of mutant $A\beta$s to the immobilized VEGF. The bound biotinylated $A\beta$ was determined with streptavidin conjugated with horse radish peroxidase. See FIG. 6 for the results.

Example 8

Heparin as Inhibitor of VEGF/$A\beta$ Interaction

Figure 7:
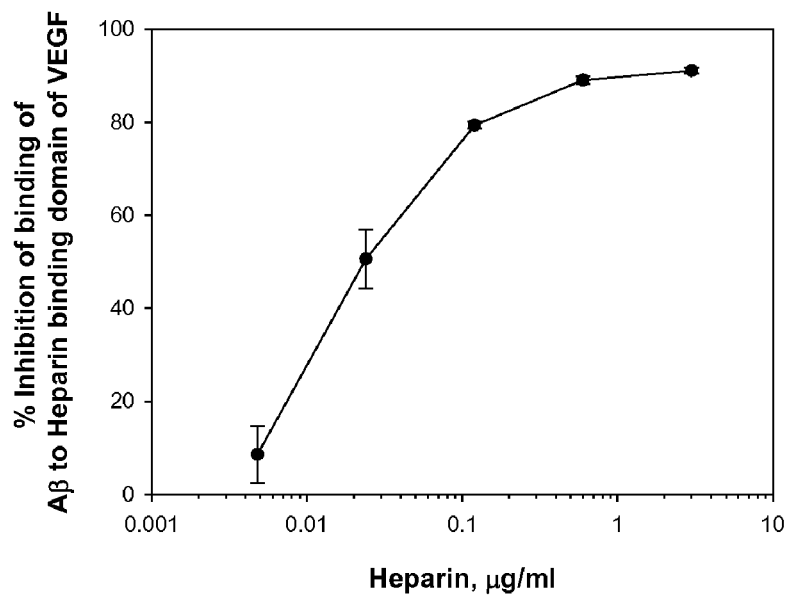
FIG. 7 shows inhibition of binding of Aβ and VEGF by heparin. GST-heparin-binding domain was immobilized on microtiter wells and binding of biotinylated Aβ1-42 in the absence, or presence of heparin was determined. As concentration of heparin increases, the binding of biotinylated Aβ to heparin-binding domain was inhibited. IC50=~25 ng/ml.

To investigate the effect of heparin on the interaction of VEGF and $A\beta$, GST-heparin-binding domain was immobilized on microtiter wells at the concentration of 100 nM, and nonspecific sites were blocked with 3% BSA/PBS. Biotinylated $A\beta_{1-42}$ (50 nM) was added to the well, alone or in the presence of increasing concentrations of heparin. After removing unbound biotinylated $A\beta$, the bound peptide was determined with steptavidin conjugated with horse radish peroxidase. See FIG. 7 for the results.

Example 9

PGG, EGCG, Tannic Acid as Inhibitors of VEGF/$A\beta$ Interaction

Figure 8:
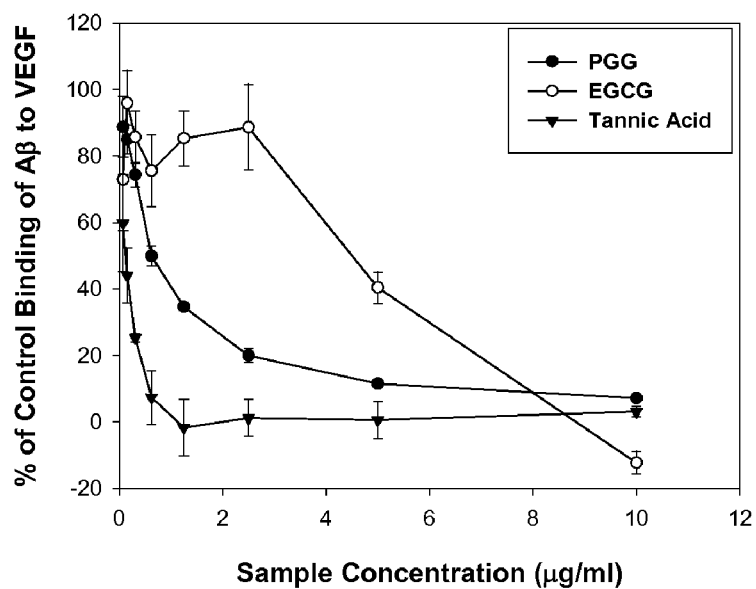
FIG. 8 shows inhibition of binding of A to VEGF by PGG, EGCG and tannic acid. VEGF165 (50 ng/well) was coated in a plastic well and biotinylated Aβ (100 ng/ml) was added in the presence of increasing concentration of PGG, EGCG or tannic acid. The biotinylated Aβ bound to VEGF165 was detected by interaction with streptavidin conjugated with horse radish peroxidase.

The inhibitory effect of PGG, EGCG and tannic acid was determined as follows: VEGF165 (50 ng/well) was coated in a plastic well, and the well was treated with 3% bovine serum albumin in PBS for 2 hours and rinsed with PBS. Biotinylated $A\beta$ (100 ng/ml) was added to each well in the presence of increasing concentration of test compound. After 2 hours, each well was rinsed several times with 0.05% Tween in PBS. The bound biotinylated $A\beta$ was determined with steptavidin conjugated with horse radish peroxidase. See FIG. 8 for the results.

All of the references cited herein are incorporated by reference in their entirety.

Example 10

Affection of VEGF or HBD on Cytotoxicity of $A\beta$

In the present invention, it is suggested the possibility that the binding of VEGF affects cytotoxicity of $A\beta$, based on the fact that VEGF binds to $A\beta$ at the amino acid region from about position 25 to about position 35 in $A\beta$, which plays an important role in cytotoxicity of $A\beta$.

Example 10.1

Investigation through MTT Assay

Figure 9A:
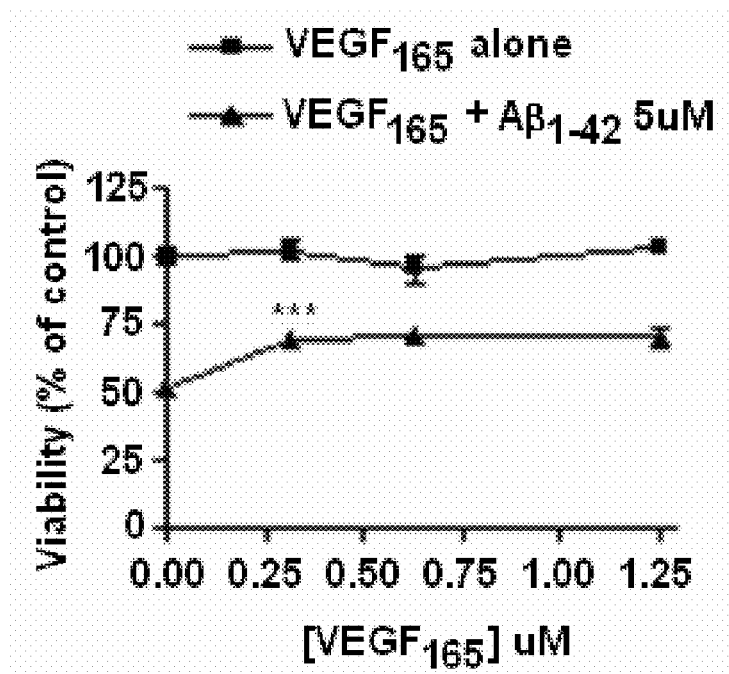
FIGS. 9A and 9B show the inhibitory effects of VEGF165 (9A) and GST-HBD (9B) on the cytotoxicity of Aβ as determined by MTT reduction.
Figure 9B:
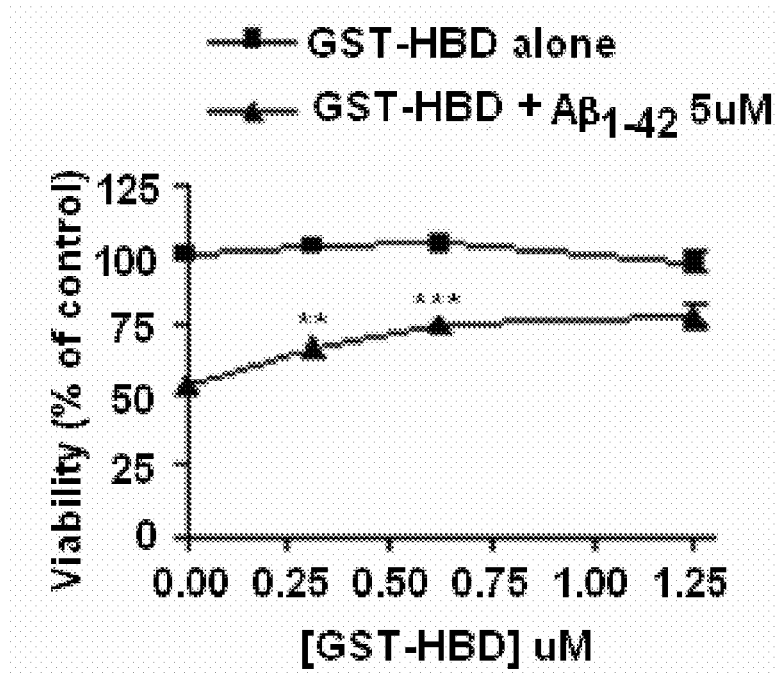

In order to such affection, this example investigated the cytotoxicity of $A\beta$ acting on the activity of reduction of PC12 cells, and the affection of VEGF thereon, to determine the viability of the cells using the conventional method of MTT [3-(4,5-dimethylthiazol-2-yl)-2,5-diphenyl-tetrazolium bromide] assay (Shearman et al., J Neurochem 65:218-227 (1995)). $VEGF_{165}$ or GST-HBD (glutathione-s-transferase labeled heparin-binding domain), each having various concentrations as shown in FIGS. 9A and 9B, and 5 pM $A\beta_{1-42}$ were mixed and incubated at 37° C. for 24 hours. The mixture was added to PC12 cells ($2 \times 10^4$, cells/well, kindly provided by Dr. Pann-Ghill Suh), and left for reaction at 37° C. for 24 hours. Then, 1/10 volume of 5 mg/ml MTT solution was added to the resulted mixture, and reacted for 2 hours. The obtained cells were lysed by 25% dimethylformamide/10% SDS. Thereafter, the absorbance of the lysate was measured at 570 nm, and then, compared with that of control of non-treated PC12 cells, to determine the reduction of MTT, and thereby determining the viability of the cells.

The results are shown in FIGS. 9A (for VEGF) and 9B (for GST-HBD). As shown in FIG. 9A, it was found that VEGF has a concentration-dependent ability to recover the activity of reduction of MTT which is deteriorated by Aβ, which shows that VEGF has the activity to inhibit the cytotoxicity of Aβ depending on the concentration thereof. As shown in FIG. 9B, HBD, which is another binder to Aβ, also exhibits the activity to inhibit the cytotoxicity of Aβ. The results shown in FIGS. 9A and 9B suggest that such inhibitory activity of VEGF to the cytotoxicity of Aβ is not caused from neurotrophic activities.

Example 10.2

Investigation through Ethidium Fluorescence Assay

Figure 10A:
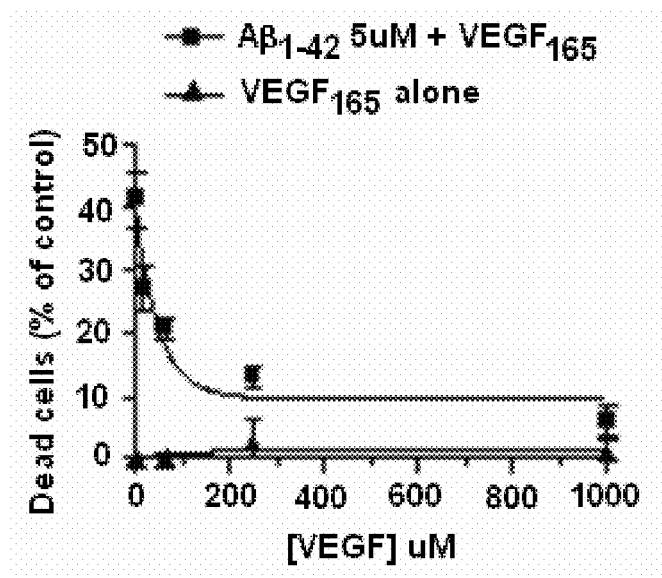
FIGS. 10A and 10B show the inhibitory effects of VEGF (10A) and GST-HBD (10B) on the cytotoxicity of Aβ as determined by binding of Ethidium homodimer-1 to DNA.
Figure 10B:
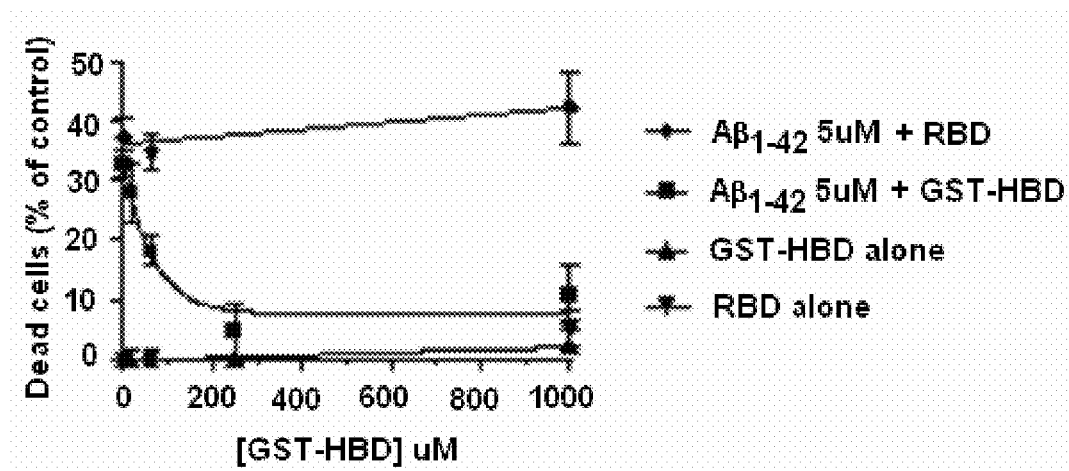

The inhibitory activity of VEGF to the cytotoxicity of Aβ was investigated by the conventional method of ethidium fluorescence assay (Qiu WQ et al., J Biol Chem 273:32730-32738 (1998)). VEGF or GST-HBD, each having various concentrations as shown in FIGS. 10A and 10B, and 5 μM $Aβ_{1-42}$ were mixed and incubated at 37° C. for 24 hours. The mixture was added to PC12 cells ($2 \times 10^4$, cells/well, kindly provided by Dr. Pann-Ghill Suh), and then left for reaction at 37° C. for 24 hours. Then, equal volume of 4 μM ethidium homodimer-1 was added to the resulted mixture, and reacted for 30 minutes. Thereafter, the fluorescence of the mixture was measured at Ex=530 nm and Em=645 nm, and then, compared with that of control of non-treated PC12 cells, to determine the cytotoxicity of Aβ.

The results are shown in FIGS. 10A (for VEGF) and 10B (for GST-HBD). The results demonstrate that both of VEGF and HBD respectively inhibit the cytotoxicity of Aβ depending on the concentration of VEGF or HBD.

Example 11

Affection of VEGF or HBD on Aggregation of Aβ

Based on the fact that the cytotoxicity of Aβ is proportional to the degree of aggregation of Aβ, and that the amino acid region from about position 25 to about position 35 in Aβ, to which VEGF binds, is also important in aggregation of Aβ, the affection of VEGF on aggregation of Aβ was investigated through the conventional method for thioflavin T assay.

Figure 11A:
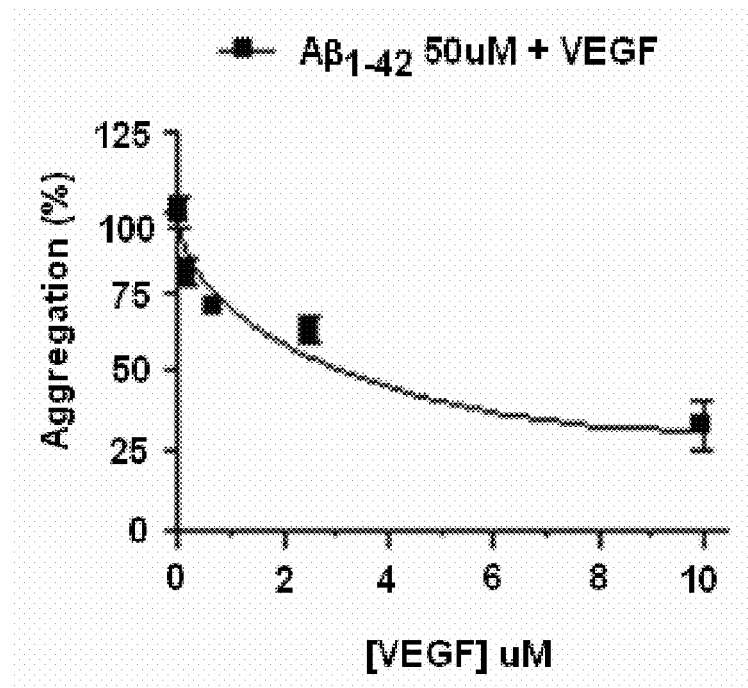
FIGS. 11A and 11B show the inhibitory effects of VEGF165 (11A) and GST-HBD (11B) on the aggregation of Aβ.
Figure 11B:
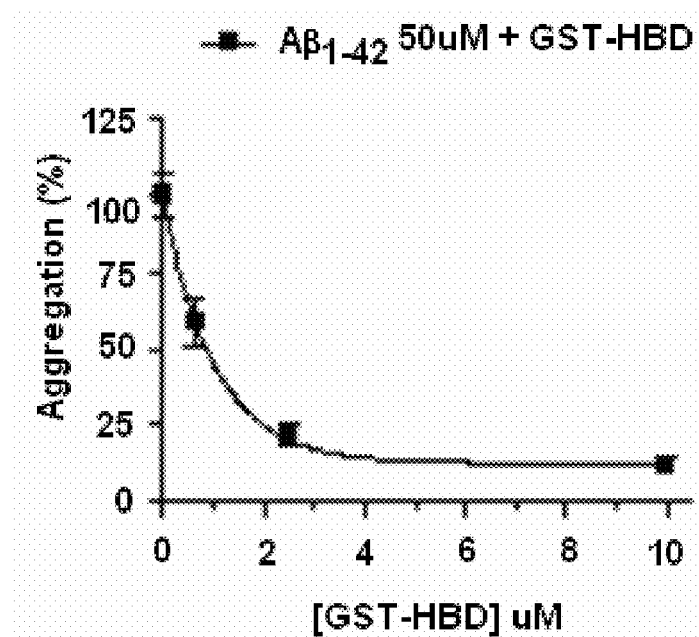

VEGF or GST-HBD, each having various concentrations as shown in FIGS. 11A and 11B, and 50 μM $Aβ_{1-42}$ were mixed and incubated at 37° C. for 24 hours. 10 μM of thioflavin T was added to the mixture and sufficiently mixed. Then, the fluorescence of the mixture was measured at Ex=444 nm and Em=485 nm, and then, compared with that of control of Aβ incubated alone, to determine the affection on aggregation of Aβ.

The results are shown in FIGS. 11A (for VEGF) and 11B (for GST-HBD). The results demonstrate that both of VEGF and HBD respectively inhibit aggregation of Aβ depending on the concentration of VEGF or HBD.

Example 12

Affection of VEGF on the Activity of Aβ to Generate Reactive Oxygen Species

Based on the fact that the mechanism of the cytotoxicity of Aβ acts mostly through generation of reactive oxygen species, the affection of VEGF on generation of reactive oxygen species by Aβ was investigated by measuring DCF (2',7'-dichlorofluorescein) fluorescence using the conventional method therefor.

5 μM $VEGF_{165}$ or 5 μM GST-HBD and 5 μM $Aβ_{1-42}$ were mixed and incubated at 37° C. for 24 hours. The mixture was added to PC12 cells ($6 \times 10^4$, cells/well, kindly provided by Dr. Pann-Ghill Suh), and then left for reaction at 37° C. for 3 hours. Then, 100 μM of DCF solution was added to the resulted mixture, reacted for 30 minutes, and then washed with PBS (phosphate-buffered saline). The obtained cells were observed through a fluorescent microscope, and DCF fluorescence was measured, to calculate the level of generation of the reactive oxygen species.

Figure 12:
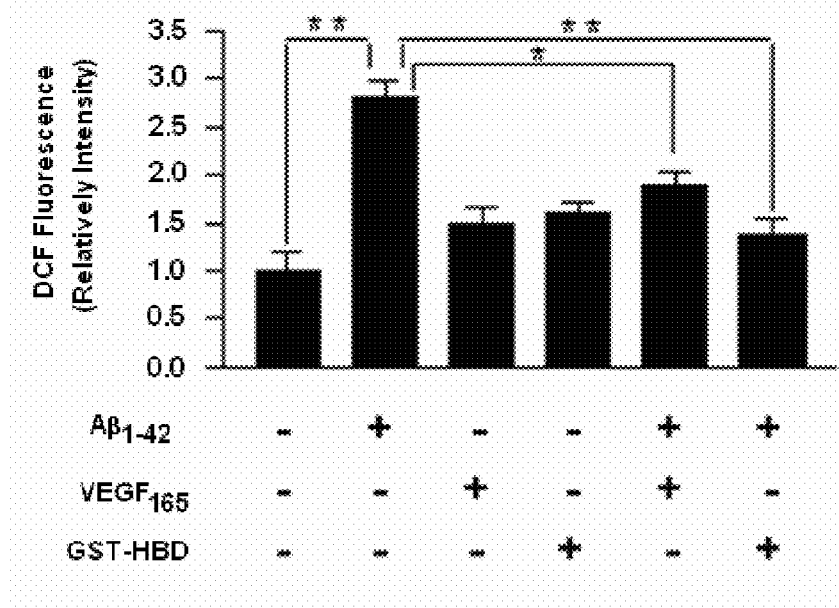
FIG. 12 shows the inhibitory effect of VEGF165 and GST-HBD on the generation of the reactive oxygen species.

The results are shown in FIG. 12. The results demonstrate that the treatment with VEGF or HBD alone exhibits no effect on the generation of the reactive oxygen species, but the treatment with VEGF or HBD together with Aβ exhibits the inhibitory effect on the generation of the reactive oxygen species by Aβ. From the results, it can be confirmed that VEGF binds to Aβ through HBD, thereby inhibits the generation of the reactive oxygen species, to inhibit the cytotoxicity of Aβ.

Example 13

Inhibition of VEGF-Aβ Binding

Example 13.1

Search for an Inhibitor of Aβ-VEGF Binding: Triamterene

Since it was found that EGCG or fucoidan, which was searched as an inhibitor of Aβ-VEGF binding, has an additional activity to inhibit the aggregation of Aβ by itself, in order to examine the affection on the Aβ-VEGF binding only, further search for other inhibitors against the Aβ-VEGF binding was conducted using a library of various drugs. As the result, triamterene was searched as the new inhibitor.

Figure 13:
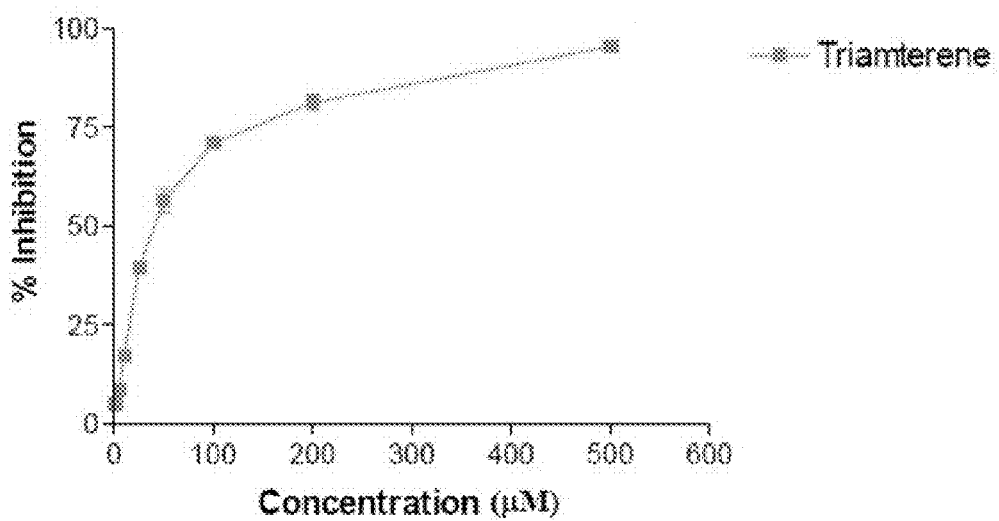
FIG. 13 shows the inhibitory effect of triamterene on the Aβ-VEGF binding.

100 nM VEGF, 100 nM biotinylated $Aβ_{1-42}$ and triamterene having various concentration as shown in FIG. 13 were mixed and incubated at 37° C. for 24 hours. The level of the formation of the Aβ-VEGF binding was measured and compared with that of control without triamterene.

The results were shown in FIG. 13. The results demonstrated that triamterene concentration-dependently inhibits the binding between Aβ and VEGF.

Example 13.2

Affection of Triamterene on the Formation of the Activities of VEGF and Aβ

In this example, it was shown that triamterene has no affection on the aggregation of Aβ and the binding between VEGF and VEGF receptor, regardless of the concentration.

Example 13.2.1

Affection on Aggregation of Aβ

Figure 14:
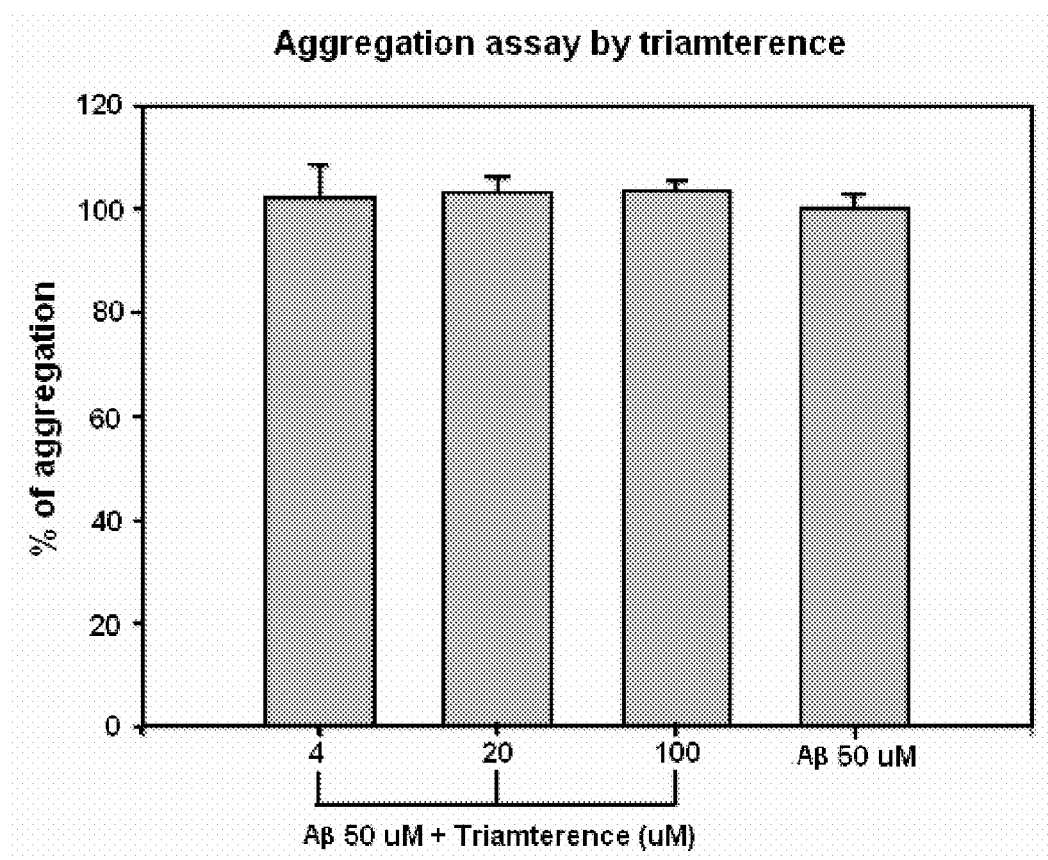
FIG. 14 shows the affection of triamterene on the aggregation of Aβ.

50 μM Aβ was incubated at 37° C. for 24 hours together with triamterene of 0 μM, 4 μM, 20 μM or 100 μM, respectively, to generate aggregation of Aβ. Then, the degree of aggregation was determined by the thioflavin T assay as illustrated in Example 11. The results are shown in FIG. 14. The results demonstrate that triamterene has no affection on aggregation of Aβ regardless of the concentration.

Example 13.2.1

Affection on VEGF-VEGF Receptor Binding

Figure 15:
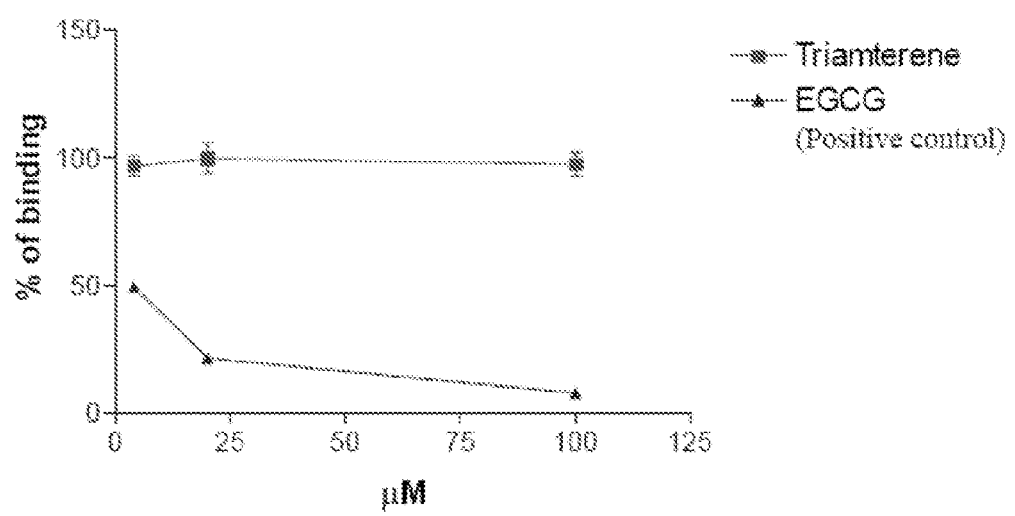
FIG. 15 shows the affection of triamterene on the VEGF-VEGF receptor binding.

VEGF was immobilized on microtiter wells at a concentration of 12 nM and nonspecific sites were blocked with 3% BSA/PBS. 0.3 nM of VEGF receptor, KDR-Fc was added to the well alone or in the presence of various concentration of triamterene, and allowed to bind to the immobilized VEGF. After removing unbound KDR-Fc, the bound KDR-Fc was determined by binding of mouse anti-Fc antibody followed by anti-mouse antibody conjugated with horse radish peroxidase. As a control, EGCG (Sigma-Aldrich, St Louis, USA) that has an inhibitory effect on the VEGF-VEGF receptor binding was used instead of triamterene. The results are shown in FIG. 15. The results demonstrate that triamterene has no affection on the VEGF-VEGF receptor binding regardless of the concentration.

Example 13.3

Analysis of the Affection of VEGF-Aβ Binding Inhibitors on VEGF Trapping

As aforementioned, the present invention suggests that the co-deposition of VEGF and Aβ decreases of the amount of soluble VEGF, resulting in a local VEGF deficiency, which is believed to contribute in deterioration of the activities of vascular cells and nerve cells. Therefore, this example was intended to investigate whether or not the VEGF-Aβ binding inhibitor, such as triamterene, can resolve the problem of VEGF deficiency due to the co-deposition of VEGF and Aβ.

For this purpose, an in vitro assay system was established. The system is simulating VEGF trapping on Aβ plaques under in vitro condition. In the in vitro assay system, 50 μM of Aβ was aggregated at 37° C. for 24 hours and immobilized on the bottom of a well by drying under air for overnight, and then, VEGF labeled with a radioisotope was added to the well, to form VEGF-Aβ binding. After removing unbound VEGF, bound VEGF was determined by measuring radioactivity. In the established system, VEGF trapping into Aβ is found in about 70% of VEGF added. The system is expected to be used in analyzing the affection of VEGF-Aβ binding inhibitors including triamterene on VEGF trapping. If certain chemical has inhibitory activity against VEGF-Aβ binding, then the chemical will decrease the amount of VEGF trapped on immobilized Aβ aggregate. And this implies that chemicals that show inhibitory activity in this system may inhibit VEGF trapping and thereby resolve the problem of VEGF deficiency in vivo.

Those skilled in the art will recognize, or be able to ascertain using no more than routine experimentation, many equivalents to the specific embodiments of the invention specifically described herein. Such equivalents are intended to be encompassed in the scope of the claims.

---

What is claimed is:

1. A method of inhibiting aggregation of β-amyloid (Aβ), comprising the steps of contacting a VEGF (Vascular endothelial growth factor) with pre-aggregated Aβ and allowing the VEGF to bind to Aβ to inhibit the aggregation of Aβ, wherein a binding site of the VEGF which binds to Aβ has the amino acid sequence of SEQ ID NO: 3.

2. The method according to claim 1, wherein a binding site of Aβ to which the VEGF binds has the amino acid sequence of SEQ ID NO: 4.

3. The method according to claim 1, which is applied to treatment of the disease selected from the group consisting of neural disease, cancer, atherosclerosis, rheumatoid arthritis, endometriosis, renal disease and obesity.

4. The method according to claim 3, wherein the neural disease is Alzheimer's Disease.

* * * * *